(12) United States Patent
Culler et al.

(10) Patent No.: US 6,268,342 B1
(45) Date of Patent: Jul. 31, 2001

(54) METHOD OF INHIBITING FIBROSIS WITH A SOMATOSTATIN AGONIST

(75) Inventors: Michael D. Culler, Hopkinton; Philip G. Kasprzyk, Boston, both of MA (US)

(73) Assignee: Biomeasure Incorporated, Milford, MA (US)

( * ) Notice: Subject to any disclaimer, the term of this patent is extended or adjusted under 35 U.S.C. 154(b) by 0 days.

(21) Appl. No.: 09/254,097

(22) PCT Filed: Aug. 27, 1997

(86) PCT No.: PCT/US97/14154

§ 371 Date: May 10, 1999

§ 102(e) Date: May 10, 1999

(87) PCT Pub. No.: WO98/08529

PCT Pub. Date: Mar. 5, 1998

Related U.S. Application Data

(63) Continuation-in-part of application No. 08/705,790, filed on Aug. 30, 1996, now abandoned.

(51) Int. Cl.[7] .............................. A61K 38/00; C07K 5/00; C07K 7/00
(52) U.S. Cl. ................... 514/12; 514/14; 530/311
(58) Field of Search ................. 514/12, 14; 530/311; 424/185.1

(56) References Cited

U.S. PATENT DOCUMENTS 4,904,642 * 2/1990 Coy et al. .............................. 514/11

OTHER PUBLICATIONS

Mizoi, T. et al., "Immunoelectron Microscopie Localization of Transforming Growth Factor Beta 1 and Latent Transforming Growth Factor Beta 1 Binding Protein in Human Gastrointestinal Carcinomas: Qualitative Difference Between Cancer Cells and Stromal Cells", Cancer Res Jan. 1, 1993; 53(1):183–190. (Abstract).
Tahara, E., "Growth Factors and Oncogenes in Human Gastrointestinal Carcinomas", J. Cancer Res. Clin. Oncol. 1990; 116(2):121–131. (Abstract).

Lyles, K.W. et al., "Peyronie's Disease is Associated with Paget's Disease of Bone", J. Bone Miner Res., Jun. 1997,; 12(6):929–934. (Abstract).
Border, W. A. et al., "Transforming Growth Factor B in Tissue Fibrosis", The New England J. of Med., vol. 331, No. 19, 1994, p. 1286–1292.
Smiley, J. D., Southwestern Internal Medical Conference: "The Many Faces of Scleroderma", Am J Med Sci 1992; 304(5)319–333.
Lundergan, C. et al., "Inhibition of Myointimal Proliferation of the Rat Carotid Artery by the Peptides, Angiopeptin and BIM 23034", Atherosclerosis, 80 (1989) 49–55.
Border, W.A. et al., "Transforming Growth Factor–Beta in Glomerular Injury", Exp Nephrol 1994;2:13–17.
Wahl, S.M., et al., Cytokine Regulation of Schistosome–induced Granuloma and Fibrosis, Kidney International, vol. 51 (1997), pp. 1370–1375.
Border et al., "Natural Inhibitor of Transforming Growth Factor–B Protects Against Scarring in Experimental Kidney Disease" Nature, V. 360, Nov. 26, 1992, pp. 361–364.
Najean, Y. et al., "Risk of Leukaemia Carcinoma and Myelofibrosis in 32P—or Chemotheraphy–treated Patients with Polycythaemia Vera: A prospective . . . ", Leuk Lymphoma, 1996, vol. 22 Suppl 1:111–119.
Tracy, T.F., Jr., et al., "Somatostatin Analogue (Octreotide) Inhibits Bile Duct Epithelial Cell Proliferation and Fibrosis After Extrahepatic Biliary Obstruction", Am J Pathol, 143(6), 1993, 1574–1578.
Tsukamoto et al., "Octerotide Treatment Results in the Inhibition of GH gene expression in the Adenoma of the Patients with Acromegaly", Endocrine Journal,, 41(4), 1994, 437–444.
Tracy et al., Am J. Pathol, 143(6) 1993 pp. 1574–1578.*
Tsukamoto et al., Endocrine Journal, 41(4), 1994, pp. 437–444.*

* cited by examiner

Primary Examiner—Avis M. Davenport
(74) Attorney, Agent, or Firm—Brian R. Morrill; Alan F. Feeney; Fish & Richardson

(57) ABSTRACT

The present invention relates to a method of inhibiting fibrosis in a patient. The method comprises administering a therapeutically effective amount of a somatostatin, a somatostatin agonist or apharmaceutically acceptable salt thereof to said patient.

29 Claims, No Drawings

METHOD OF INHIBITING FIBROSIS WITH A SOMATOSTATIN AGONIST

This application is a 371 of PCT/US97/14154 filed Aug. 27, 1997 which is a continuation-in-part of Ser. No. 08/705,790 filed Aug. 30, 1996 now abandoned.

BACKGROUND OF THE INVENTION

Tissue comprises organized cellular groups that are attached to an extracellular matrix and are surrounded by a network of blood vessels. Fibrosis is an abnormal accumulation of a collagen matrix following injury or inflammation which alters the structure and function of various tissues. Irrespective of location, the major pathology of fibrosis involves an excessive deposition of a collagen matrix which replaces the normal tissue at that site. Progressive fibrosis in the kidney, liver, lung, heart, bone or bone marrow, and skin is a major cause of death and suffering. See, e.g., Border, et al., New Engl. J. Med. 331:1286 (1994).

Development of fibrosis has been linked to the overexpression and over-production of TGF-$\beta$ in numerous tissues and fibrotic disease states (see Border et al., N Engl J Med 1994, pp. 1286–92).

SUMMARY OF THE INVENTION

The present invention relates to a method of treating fibrosis in a patient (e.g., a mammal such as a human). The method includes the step of administering a therapeutically effective amount of somatostatin or a somatostatin agonist to said patient. The somatostatin or somatostatin agonist may be administered orally, topically, parenterally, e.g., administered intravenously, subcutaneously, or by implantation of a sustained release formulation. Fibrosis is the abnormal accumulation of an extracellular matrix (e.g., collagen) in tissue. The fibrosis, for example, may be located: in the kidney, for example, fibrosis as observed in glomerulonenephritis, diabetic nephropathy), allograft rejection, and HIV nephropathy; in the liver, for example, cirrhosis, and veno-occlusive disease; in the lung, for example, idiopathic fibrosis; in the skin, for example, systemic sclerosis, keloids, scars, and eosinophilia-myalgia syndrome; in the central nervous system, for example, intraocular fibrosis; in the cardiovascular system, for example, vascular restenosis; in the nose, for example, nasal polyposis; in bone or bone marrow; in an endocrine organ; and in the gastrointestinal system.

A fibrotic disorder may be induced by a number of causes including: chemotherapy, for example pulmonary fibrosis resulting from bleomycin, chlorambucil, cyclophspamide, methotrexate, mustine, or procarbazine treatment; radiation exposure whether accidental or purposeful as in radiation therapy, for example, interstitial lung disease (ILD) resulting from radiation; environmental or industrial factors or pollutants such as chemicals, fumes, metals, vapors, gases, etc.(e.g. ILD resulting from asbestos or coal dust); a drug or combination of drugs, for example, antibiotics (e.g. penicillins, sulfonamides, etc.), cardiovascular drugs (e.g. hydralazine, beta blockers, etc.), CNS drugs (phenytoin, chlorpromazine, etc.) anti-inflammatory drugs (e.g. gold salts, phenylbutazone, etc.), etc. can cause ILD; an immune reaction disorder, for example, chronic graft-vs-host disease with dermal fibrosis); disease states (e.g., aspiration pneumonia which is a known cause of ILD) which include parasite induced fibrosis; and wounds, for example, blunt trauma, surgical incisions, battlefield wounds, etc., as in penetrating injuries of the CNS.

In one aspect, this invention provides a method of inhibiting fibrosis in a patient, said method comprising administering a therapeutically effective amount of somatostatin or a somatostatin agonist to said patient; a method which is preferred of the foregoing method is wherein said method comprises administering a therapeutically effective amount of a somatostatin agonist to said patient.

In another aspect, this invention provides a method of inhibiting fibrosis in a patient which comprises administering to the patient a therapeutically effective amount of a somatostatin agonist wherein the fibrosis which is inhibited is in the: kidney wherein the fibrotic disorder inhibited in the kidney is preferably glomerulonephritis, diabetic nephropathy, allograft rejection or HIV nephropathy, lung wherein the fibrotic disorder inhibited in the lung is preferably idiopathic fibrosis or autoimmune fibrosis, liver wherein the fibrotic disorder inhibited in the liver is preferably cirrhosis or veno-occlusive disease, skin wherein the fibrotic disorder inhibited in the skin is preferably systemic sclerosis, keloids, scars or eosinophilia-myalgia syndrome, central nervous system wherein the fibrotic disorder inhibited in the central nervous system is preferably intraocular fibrosis, bone or bone marrow, cardiovascular system, an endocrine organ or gastrointestinal system. Each of the immediately foregoing methods is preferred.

In yet another aspect, this invention provides a method of inhibiting fibrosis in a patient which comprises administering to the patient a therapeutically effective amount of a somatostatin agonist wherein the fibrosis is induced by chemotherapy and preferably the fibrosis inhibited is in the kidney, lung, liver, skin, central nervous system, bone or bone marrow, cardiovascular system, an endocrine organ or gastrointestinal system. Each of the immediately foregoing methods is preferred.

In yet another aspect, this invention provides a method of inhibiting fibrosis in a patient which comprises administering to the patient a therapeutically effective amount of a somatostatin agonist wherein the fibrosis is induced by radiation and preferably the fibrosis inhibited is in the kidney, lung, liver, skin, central nervous system, bone or bone marrow, cardiovascular system, an endocrine organ or gastrointestinal system. Each of the immediately foregoing methods is preferred.

In yet another aspect, this invention provides a method of inhibiting fibrosis in a patient which comprises administering to the patient a therapeutically effective amount of a somatostatin agonist wherein the fibrosis is induced by a drug or combination of drugs and preferably the fibrosis inhibited is in the kidney, lung, liver, skin, central nervous system, bone or bone marrow, cardiovascular system, an endocrine organ or gastrointestinal system. Each of the immediately foregoing methods is preferred.

In yet another aspect, this invention provides a method of inhibiting fibrosis in a patient which comprises administering to the patient a therapeutically effective amount of a somatostatin agonist wherein the fibrosis is induced by a disease state and preferably the fibrosis inhibited is in the kidney, lung, liver, skin, central nervous system, bone or bone marrow, cardiovascular system, an endocrine organ or gastrointestinal system. Each of the immediately foregoing methods is preferred.

In yet another aspect, this invention provides a method of inhibiting fibrosis in a patient which comprises administering to the- patient a therapeutically effective amount of a somatostatin agonist wherein the fibrosis is induced by an environmental or industrial factor and preferably the fibrosis inhibited is in the kidney, lung, liver, skin, central nervous system, bone or bone marrow, cardiovascular system, an endocrine organ or gastrointestinal system. Each of the immediately foregoing methods is preferred.

In yet another aspect, this invention provides a method of inhibiting fibrosis in a patient which comprises administering to the patient a therapeutically effective amount of a somatostatin agonist wherein the fibrosis is induced by an immune response by the patient and preferably the fibrosis inhibited is in the kidney, lung, liver, skin, central nervous system, bone or bone marrow, cardiovascular system, an endocrine organ or gastrointestinal system. Each of the immediately foregoing methods is preferred.

In yet another aspect, this invention provides a method of inhibiting fibrosis in a patient which comprises administering to the patient a therapeutically effective amount of a somatostatin agonist wherein the fibrosis is induced by a wound and preferably the fibrosis inhibited is in the kidney, lung, liver, skin, central nervous system, bone or bone marrow, cardiovascular system, an endocrine organ or gastrointestinal system. Each of the immediately foregoing methods is preferred.

In still another aspect, this invention provides a method of inhibiting fibrosis in a patient which comprises administering to the patient a therapeutically effective amount of a somatostatin agonist wherein the somatostatin agonist has a higher binding affinity for human somatostatin sub-type receptor 1 than the other human somatostatin sub-type receptors, for human somatostatin sub-type receptor 2 than the other human somatostatin sub-type receptors, for human somatostatin sub-type receptor 3 than the other human somatostatin sub-type receptors for human somatostatin sub-type receptor 4 than the other human somatostatin sub-type receptors, or for human somatostatin sub-type receptor 5 than the other human somatostatin sub-type receptors; or wherein the somatostatin agonist has a higher binding affinity for two or more of human somatostatin receptor sub-types e.g., 1, 2, 3, 4 and/or 5. Each of the immediately forgoing methods is preferred.

In still another aspect, this invention provides a method of inhibiting fibrosis in a patient which comprises administering to the patient a therapeutically effective amount of a somatostatin agonist wherein the somatostatin agonist is

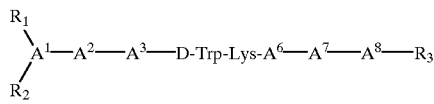

or a pharmaceutically acceptable salt thereof, wherein $A^1$ is a D- or L- isomer of Ala, Leu, Ile, Val, Nle, Thr, Ser, β-Nal, β-Pal, Trp, Phe, 2,4-dichloro-Phe, pentafluoro-Phe, p-X-Phe, or o-X-Phe;

$A^2$ is Ala, Leu, Ile, Val, Nle, Phe, β-Nal, pyridyl-Ala, Trp, 2,4-dichloro-Phe, pentafluoro-Phe, o-X-Phe, or p-X-Phe;

$A^3$ is pyridyl-Ala, Trp, Phe, β-Nal, 2,4-dichloro-Phe, pentafluoro-Phe, o-X-Phe, or p-X-Phe;

$A^6$ is Val, Ala, Leu, Ile, Nle, Thr, Abu, or Ser;

$A^7$ is Ala, Leu, Ile, Val, Nle, Phe, β-Nal, pyridyl-Ala, Trp, 2,4-dichloro-Phe, pentafluoro-Phe, o-X-Phe, or p-X-Phe;

$A^8$ is a D- or L-isomer of Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe;

wherein X for each occurrence is independently selected from the group consisting of $CH_3$, Cl, Br, F, OH, $OCH_3$ and $NO_2$;

each $R_1$ and $R_2$, independently, is H, lower acyl or lower alkyl; and $R_3$ is OH or $NH_2$; provided that at least one of $A^1$ and $A^8$ and one of $A^2$ and $A^7$ must be an aromatic amino acid; and further provided that $A^1$, $A^2$, $A^7$ and $A^8$ cannot all be aromatic amino acids.

In still another aspect, a method of inhibiting fibrosis in a patient which comprises administering to the patient a therapeutically effective amount of a somatostatin agonist wherein the somatostatin agonist is H-D-Phe-p-chloro-Phe-Tyr-D-Trp-Lys-Thr-Phe-Thr-$NH_2$;
H-D-Phe-p-$NO_2$-Phe-Tyr-D-Trp-Lys-Val-Phe-Thr-$NH_2$;
H-D-Nal-p-chloro-Phe-Tyr-D-Trp-Lys-Val-Phe-Thr-$NH_2$;
H-D-Phe-Phe-Phe-D-Trp-Lys-Thr-Phe-Thr-$NH_2$;
H-D-Phe-Phe-Tyr-D-Trp-Lys-Val-Phe-Thr-$NH_2$;
H-D-Phe-p-chloro-Phe-Tyr-D-Trp-Lys-Val-Phe-Thr-$NH_2$; or
H-D-Phe-Ala-Tyr-D-Trp-Lys-Val-Ala-β-D-Nal-$NH_2$ or a pharmaceutically acceptable salt thereof.

In still another aspect, a method of inhibiting fibrosis in a patient which comprises administering to the patient a therapeutically effective amount of a somatostatin agonist wherein the somatostatin agonist is D-Phe-Cys-Phe-D-Trp-Lys-Thr-Cys-β-Nal-$NH_2$;
D-Phe-Cys-Tyr-D-Trp-Lys-Thr-Cys-β-Nal-$NH_2$;
D-β-Nal-Cys-Phe-D-Trp-Lys-Thr-Cys-Thr-$NH_2$;
D-Phe-Cys-Tyr-D-Trp-Lys-Thr-Pen-Thr-$NH_2$;
D-Phe-Cys-Phe-D-Trp-Lys-Thr-Pen-Thr-$NH_2$;
D-Phe-Cys-Tyr-D-Trp-Lys-Thr-Pen-Thr-OH;
D-Phe-Cys-Phe-D-Trp-Lys-Thr-Pen-Thr-OH;
Gly-Pen-Phe-D-Trp-Lys-Thr-Cys-Thr-OH;
Phe-Pen-Tyr-D-Trp-Lys-Thr-Cys-Thr-OH;
Phe-Pen-Phe-D-Trp-Lys-Thr-Pen-Thr-OH;
H-D-Phe-Cys-Phe-D-Trp-Lys-Thr-Cys-Thr-ol;
H-D-Phe-Cys-Phe-D-Trp-Lys-Thr-Cys-Thr-$NH_2$;
H-D-Trp-Cys-Tyr-D-Trp-Lys-Val-Cys-Thr-$NH_2$;
H-D-Trp-Cys-Phe-D-Trp-Lys-Thr-Cys-Thr-$NO_2$;
H-D-Phe-Cys-Tyr-D-Trp-Lys-Val-Cys-Thr-$NH_2$;
H-D-Phe-Cys-Tyr-D-Trp-Lys-Val-Cys-Trp-$NH_2$;
H-D-Phe-Cys-Tyr-D-Trp-Lys-Val-Cys-Thr-$NH_2$;
Ac-D-Phe-Lys*-Tyr-D-Trp-Lys-Val-Asp-Thr-$NH_2$, wherein an amide bridge is between Lys* and Asp;
Ac-hArg(Et)$_2$-Gly-Cys-Phe-D-Trp-Lys-Thr-Cys-Thr-$NH_2$;
Ac-D-hArg(Et)2-Gly-Cys-Phe-D-Trp-Lys-Thr-Cys-Thr-$NH_2$;
Ac-D-hArg(Bu)-Gly-Cys-Phe-D-Trp-Lys-Thr-Cys-Thr-$NH_2$;
Ac-D-hArg(Et)$_2$-Cys-Phe-D-Trp-Lys-Thr-Cys-Thr-$NH_2$;
Ac-L-hArg (Et)$_2$-Cys-Phe-D-Trp-Lys-Thr-Cys-Thr-$NH_2$;
Ac-D-hArg ($CH_2CF_3$)$_2$-Cys-Phe-D-Trp-Lys-Thr-Cys-Thr-$NH_2$;
Ac-D-hArg ($CH_2CF_3$)$_2$-Gly-Cys-Phe-D-Trp-Lys-Thr-Cys-Thr-$NH_2$;
Ac-D-hArg ($CH_2CF_3$)$_2$-Gly-Cys-Phe-D-Trp-Lys-Thr-Cys-Phe-$NH_2$;
Ac-D-hArg ($CH_2CF_3$)$_2$-Gly-Cys-Phe-D-Trp-Lys-Thr-Cys-Thr-NHEt;
Ac-L-hArg ($CH_2$-$CF_3$)$_2$-Gly-Cys-Phe-D-Trp-Lys-Thr-Cys-Thr-$NH_2$;
Ac-D-hArg ($CH_2CF_3$)$_2$-Gly-Cys-Phe-D-Trp-Lys (Me) -Thr-Cys-Thr-$NH_2$;
Ac-D-hArg ($CH_2CF_3$)$_2$-Gly-Cys-Phe-D-Trp-Lys(Me)-Thr-Cys-Thr-NHEt;
Ac-hArg ($CH_3$, hexyl)-Gly-Cys-Phe-D-Trp-Lys-Thr-Cys-Thr-$NH_2$;
H-hArg (hexyl)$_2$-Gly-Cys-Phe-D-Trp-Lys-Thr-Cys-Thr-$NH_2$;
Ac-D-hArg (Et)$_2$-Gly-Cys-Phe-D-Trp-Lys-Thr-Cys-Thr-NHEt;

Ac-D-hArg(Et)$_2$-Gly-Cys-Phe-D-Trp-Lys-Thr-Cys-Phe-NH$_2$;
Propionyl-D-hArg (Et) $_2$-Gly-Cys-Phe-D-Trp-Lys(iPr)-Thr-Cys-Thr-NH$_2$;
Ac-D-β-Nal-Gly-Cys-Phe-D-Trp-Lys-Thr-Cys-Gly-hArg (Et)$_2$-NH$_2$;
Ac-D-Lys(iPr)-Gly-Cys-Phe-D-Trp-Lys-Thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-Thr-Cys-Phe-NH$_2$;
Ac-D-hArg(Et)$_2$-D-hArg(Et)$_2$-Gly-Cys-Phe-D-Trp-Lys-Thr-Cys-Thr-NH$_2$;
Ac-Cys-Lys-Asn-4-Cl-Phe-Phe-D-Trp-Lys-Thr-Phe-Thr-Ser-D-Cys-NH$_2$;
Bmp-Tyr-D-Trp-Lys-Val-Cys-Thr-NH$_2$;
Bmp-Tyr-D-Trp-Lys-Val-Cys-Phe-NH$_2$;
Bmp-Tyr-D-Trp-Lys-Val-Cys-p-Cl-Phe-NH$_2$;
Bmp-Tyr-D-Trp-Lys-Val-Cys-β-Nal-NH$_2$;
H-D-β-Nal-Cys-Tyr-D-Trp-Lys-Val-Cys-Thr-NH$_2$;
H-D-Phe-Cys-Tyr-D-Trp-Lys-Abu-Cys-Thr-NH$_2$;
H-D-Phe-Cys-Tyr-D-Trp-Lys-Abu-Cys-β-Nal-NH$_2$;
H-pentafluoro-D-Phe-Cys-Tyr-D-Trp-Lys-Val-Cys-Thr-NH$_2$;
Ac-D-β-Nal-Cys-pentafluoro-Phe-D-Trp-Lys-Val-Cys-Thr-NH$_2$;
H-D-β-Nal-Cys-Tyr-D-Trp-Lys-Val-Cys-β-Nal-NH$_2$;
H-D-Phe-Cys-Tyr-D-Trp-Lys-Val-Cys-β-Nal-NH$_2$;
H-D-β-Nal-Cys-Tyr-D-Trp-Lys-Abu-Cys-Thr-NH$_2$;
H-D-p-Cl-Phe-Cys-Tyr-D-Trp-Lys-Abu-Cys-Thr-NH$_2$;
Ac-D-p-Cl-Phe-Cys-Tyr-D-Trp-Lys-Abu-Cys-Thr-NH$_2$;
H-D-Phe-Cys-β-Nal-D-Trp-Lys-Val-Cys-Thr-NH$_2$;
H-D-Phe-Cys-Tyr-D-Trp-Lys-Cys-Thr-NH$_2$;
cyclo (Pro-Phe-D-Trp-N-Me-Lys-Thr-Phe);
cyclo (Pro-Phe-D-Trp-N-Me-Lys-Thr-Phe);
cyclo (Pro-Phe-D-Trp-Lys-Thr-N-Me-Phe);
cyclo (N-Me-Ala-Tyr-D-Trp-Lys-Thr-Phe);
cyclo (Pro-Tyr-D-Trp-Lys-Thr-Phe);

cyclo (Asn-Phe-D-Trp-Lys-Thr-Phe);
cyclo (Asn-Phe-D-Trp-Lys-Thr-Phe-NH(CH$_2$)$_4$CO);
cyclo (Asn-Phe-D-Trp-Lys-Thr-Phe-β-Ala);
cyclo (Asn-Phe-D-Trp-Lys-Thr-Phe-D-Glu)-OH;
cyclo (Phe-Phe-D-Trp-Lys-Thr-Phe);
cyclo (Phe-Phe-D-Trp-Lys-Thr-Phe-Gly);
cyclo (Phe-Phe-D-Trp-Lys-Thr-Phe-Gaba);
cyclo (Asn-Phe-Phe-D-Trp-Lys-Thr-Phe-Gly);
cyclo (Asn-Phe-Phe-D-Trp(F)-Lys-Thr-Phe-Gaba);
cyclo (Asn-Phe-Phe-D-Trp (NO$_2$) -Lys-Thr-Phe-Gaba);
cyclo (Asn-Phe-Phe-Trp(Br)-Lys-Thr-Phe-Gaba);
cyclo (Asn-Phe-Phe-D-Trp-Lys-Thr-Phe(I)-Gaba);
cyclo (Asn-Phe-Phe-D-Trp-Lys-Thr-Tyr(But)-Gaba);
cyclo (Bmp-Lys-Asn-Phe-Phe-D-Trp-Lys-Thr-Phe-Thr-Pro-Cys)-OH;
cyclo (Bmp-Lys-Asn-Phe-Phe-D-Trp-Lys-Thr-Phe-Thr-Pro-Cys)-OH;
cyclo (Bmp-Lys-Asn-Phe-Phe-D-Trp-Lys-Thr-Phe-Thr-Tpo-Cys)-OH;
cyclo (Bmp-Lys-Asn-Phe-Phe-D-Trp-Lys-Thr-Phe-Thr-MeLeu-Cys)-OH;
cyclo (Phe-Phe-D-Trp-Lys-Thr-Phe-Phe-Gaba);
cyclo (Phe-Phe-D-Trp-Lys-Thr-Phe-D-Phe-Gaba);
cyclo (Phe-Phe-D-Trp(5F)-Lys-Thr-Phe-Phe-Gaba);
cyclo (Asn-Phe-Phe- D-Trp-Lys(Ac)-Thr-Phe-NH-(CH$_2$)$_3$-CO);
cyclo (Lys-Phe-Phe-D-Trp-Lys-Thr-Phe-Gaba);
cyclo (Lys-Phe-Phe-D-Trp-Lys-Thr-Phe-Gaba); or
cyclo (Orn-Phe-Phe-D-Trp-Lys-Thr-Phe-Gaba) or a pharmaceutically acceptable salt thereof.

In still another aspect, a method of inhibiting fibrosis in a patient which comprises administering to the patient a therapeutically effective amount of a somatostatin agonist wherein the somatostatin agonist is D-β-Nal-Cys-Tyr-D-Trp-Lys-Thr-Cys-Thr-NH$_2$, H-Cys-Phe-Phe-D-Trp-Lys-Thr-Phe-Cys-NH$_2$,

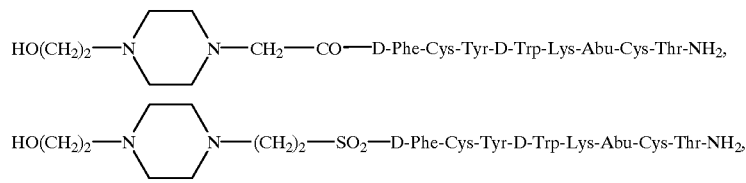

cyclo (Pro-Phe-D-Trp-Lys-Thr-Phe);
cyclo (Pro-Phe-L-Trp-Lys-Thr-Phe);
cyclo (Pro-Phe-D-Trp(F)-Lys-Thr-Phe);
cyclo (Pro-Phe-Trp(F)-Lys-Thr-Phe);
cyclo (Pro-Phe-D-Trp-Lys-Ser-Phe);
cyclo (Pro-Phe-D-Trp-Lys-Thr-p-Cl-Phe);
cyclo (D-Ala-N-Me-D-Phe-D-Thr-D-Lys-Trp-D-Phe);
cyclo (D-Ala-N-Me-D-Phe-D-Val-Lys-D-Trp-D-Phe);
cyclo (D-Ala-N-Me-D-Phe-D-Thr-Lys-D-Trp-D-Phe);
cyclo (D-Abu-N-Me-D-Phe-D-Val-Lys-D-Trp-D-Tyr);
cyclo (Pro-Tyr-D-Trp-t-4-AchxAla-Thr-Phe);
cyclo (Pro-Phe-D-Trp-t-4-AchxAla-Thr-Phe);
cyclo (N-Me-Ala-Tyr-D-Trp-Lys-Val-Phe);
cyclo (N-Me-Ala-Tyr-D-Trp-t-4-AchxAla-Thr-Phe);
cyclo (Pro-Tyr-D-Trp-4-Amphe-Thr-Phe);
cyclo (Pro-Phe-D-Trp-4-Amphe-Thr-Phe);
cyclo (N-Me-Ala-Tyr-D-Trp-4-Amphe-Thr-Phe);
cyclo (Asn-Phe-Phe-D-Trp-Lys-Thr-Phe-Gaba);
cyclo (Asn-Phe-Phe-D-Trp-Lys-Thr-Phe-Gaba-Gaba);

or D-Phe-cyclo(Cys-Phe-D-Trp-Lys-Thr-Cys)-Thr-ol or a pharmaceutically acceptable salt thereof. Each of the immediately foregoing methods is preferred.

In a further aspect, this invention provides a method of inhibiting overexpression of TGF-β which comprises administering to a subject an effective amount of somatostatin, somatostatin agonist or a pharmaceutically acceptable salt thereof; preferred of this method is where a somatostatin agonist is administered; a preferred method of the immediately foregoing method is wherein the somatostatin agonist has a higher binding affinity for human somatostatin sub-type receptor 1 than the other human somatostatin sub-type receptors, human somatostatin sub-type receptor 2 than the other human somatostatin sub-type receptors, human somatostatin sub-type receptor 3 than the other human somatostatin sub-type receptors, human somatostatin sub-type receptor 4 than the other human somatostatin sub-type receptors or human somatostatin sub-type receptor 5 than the other human somatostatin sub-type receptors; or wherein the somatostatin agonist has a higher binding affinity for two or more of human somatostatin receptor sub-types e.g., 1, 2, 3, 4 and/or 5. Each of the foregoing methods is preferred.

In another further aspect, this invention provides a method of inhibiting overexpression of TGF-β which comprises administering to a subject an effective amount of a somatostatin agonist wherein the somatostatin agonist is

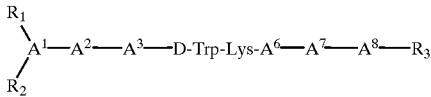

or a pharmaceutically acceptable salt thereof, wherein
$A^1$ is a D- or L- isomer of Ala, Leu, Ile, Val, Nle, Thr, Ser, β-Nal, β-Pal, Trp, Phe, 2,4-dichloro-Phe, pentafluoro-Phe, p-X-Phe, or o-X-Phe;
$A^2$ is Ala, Leu, Ile, Val, Nle, Phe, β-Nal, pyridyl-Ala, Trp, 2,4-dichloro-Phe, pentafluoro-Phe, o-X-Phe, or p-X-Phe;
$A^3$ is pyridyl-Ala, Trp, Phe, β-Nal, 2,4-dichloro-Phe, pentafluoro-Phe, o-X-Phe, or p-X-Phe;
$A^6$ is Val, Ala, Leu, Ile, Nle, Thr, Abu, or Ser;
$A^7$ is Ala, Leu, Ile, Val, Nle, Phe, β-Nal, pyridyl-Ala, Trp, 2,4-dichloro-Phe, pentafluoro-Phe, o-X-Phe, or p-X-Phe;
$A^8$ is a D- or L-isomer of Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe;
wherein X for each occurrence is independently selected from the group consisting of $CH_3$, Cl, Br, F, OH, $OCH_3$ and $NO_2$;
each $R_1$ and $R_2$, independently, is H, lower acyl or lower alkyl; and $R_3$ is OH or $NH_2$; provided that at least one of $A^1$ and $A^8$ and one of $A^2$ and $A^7$ must be an aromatic amino acid; and further provided that $A^1$, $A^2$, $A^7$ and $A^8$ cannot all be aromatic amino acids.

Also, this invention provides a method of inhibiting overexpression of TGF-β which comprises administering to a subject an effective amount of somatostatin agonist wherein the somatostatin agonist is
H-D-Phe-p-chloro-Phe-Tyr-D-Trp-Lys-Thr-Phe-Thr-NH₂;
H-D-Phe-p-NO₂-Phe-Tyr-D-Trp-Lys-Val-Phe-Thr-NH₂;
H-D-Nal-p-chloro-Phe-Tyr-D-Trp-Lys-Val-Phe-Thr-NH₂;
H-D-Phe-Phe-Phe-D-Trp-Lys-Thr-Phe-Thr-NH₂;
H-D-Phe-Phe-Tyr-D-Trp-Lys-Val-Phe-Thr-NH₂;
H-D-Phe-p-chloro-Phe-Tyr-D-Trp-Lys-Val-Phe-Thr-NH₂; or
H-D-Phe-Ala-Tyr-D-Trp-Lys-Val-Ala-β-D-Nal-NH₂ or a pharmaceutically acceptable salt thereof.

Also, this invention provides a method of inhibiting overexpression of TGF-β which comprises administering to a subject an effective amount of somatostatin agonist wherein the somatostatin agonist is
D-Phe-Cys-Phe-D-Trp-Lys-Thr-Cys-β-Nal-NH₂;
D-Phe-Cys-Tyr-D-Trp-Lys-Thr-Cys-β-Nal-NH₂;
D-β-Nal-Cys-Phe-D-Trp-Lys-Thr-Cys-Thr-NH₂;
D-Phe-Cys-Tyr-D-Trp-Lys-Thr-Pen-Thr-NH₂;
D-Phe-Cys-Phe-D-Trp-Lys-Thr-Pen-Thr-NH₂;
D-Phe-Cys-Tyr-D-Trp-Lys-Thr-Pen-Thr-OH;
D-Phe-Cys-Phe-D-Trp-Lys-Thr-Pen-Thr-OH;
Gly-Pen-Phe-D-Trp-Lys-Thr-Cys-Thr-OH;
Phe-Pen-Tyr-D-Trp-Lys-Thr-Cys-Thr-OH;
Phe-Pen-Phe-D-Trp-Lys-Thr-Pen-Thr-OH;
H-D-Phe-Cys-Phe-D-Trp-Lys-Thr-Cys-Thr-ol;
H-D-Phe-Cys-Phe-D-Trp-Lys-Thr-Cys-Thr-NH₂;
H-D-Trp-Cys-Tyr-D-Trp-Lys-Val-Cys-Thr-NH₂;
H-D-Trp-Cys-Phe-D-Trp-Lys-Thr-Cys-Thr-NH₂;
H-D-Phe-Cys-Tyr-D-Trp-Lys-Val-Cys-Thr-NH₂;
H-D-Phe-Cys-Tyr-D-Trp-Lys-Val-Cys-Trp-NH₂;
H-D-Phe-Cys-Tyr-D-Trp-Lys-Val-Cys-Thr-NH₂;
Ac-D-Phe-Lys*-Tyr-D-Trp-Lys-Val-Asp-Thr-NH₂, wherein an amide bridge is between Lys* and Asp;
Ac-hArg(Et)₂-Gly-Cys-Phe-D-Trp-Lys-Thr-Cys-Thr-NH₂;
Ac-D-hArg (Et)₂-Gly-Cys-Phe-D-Trp-Lys-Thr-Cys-Thr-NH₂;
Ac-D-hArg(Bu)-Gly-Cys-Phe-D-Trp-Lys-Thr-Cys-Thr-NH₂;
Ac-D-hArg(Et)₂-CYS-Phe-D-Trp-Lys-Thr-Cys-Thr-NH₂;
Ac-L-hArg(Et)₂-Cys-Phe-D-Trp-Lys-Thr-Cys-Thr-NH₂;
Ac-D-hArg (CH₂CF₃)₂-Cys-Phe-D-Trp-Lys-Thr-Cys-Thr-NH₂;
Ac-D-hArg(CH₂CF₃)₂-Gly-Cys-Phe-D-Trp-Lys-Thr-Cys-Thr-NH₂;
Ac-D-hArg(CH₂CF₃)₂-Gly-Cys-Phe-D-Trp-Lys-Thr-Cys-Phe-NH₂;
Ac-D-hArg(CH₂CF₃)₂-Gly-Cys-Phe-D-Trp-Lys-Thr-Cys-Thr-NHEt;
Ac-L-hArg(CH₂-CF₃)₂-Gly-Cys-Phe-D-Trp-Lys-Thr-Cys-Thr-NH₂;
Ac-D-hArg(CH₂CF₃)₂-Gly-Cys-Phe-D-Trp-Lys(Me)-Thr-Cys-Thr-NH₂;
Ac-D-hArg(CH₂CF₃)₂-Gly-Cys-Phe-D-Trp-Lys(Me)-Thr-Cys-Thr-NHEt;
Ac-hArg(CH₃, hexyl)-Gly-Cys-Phe-D-Trp-Lys-Thr-Cys-Thr-NH₂;
H-hArg (hexyl₂)-Gly-Cys-Phe-D-Trp-Lys-Thr-Cys-Thr-NH₂;
Ac-D-hArg (Et)₂-Gly-Cys-Phe-D-Trp-Lys-Thr-Cys-Thr-NHEt;
Ac-D-hArg (Et)₂-Gly-Cys-Phe-D-Trp-Lys-Thr-Cys-Phe-NH₂;
Propionyl-D-hArg (Et)₂-Gly-Cys-Phe-D-Trp-Lys(iPr)-Thr-Cys-Thr-NH₂;
Ac-D-β-Nal-Gly-Cys-Phe-D-Trp-Lys-Thr-Cys-Gly-hArg (Et)₂-NH₂;
Ac-D-Lys(iPr)-Gly-Cys-Phe-D-Trp-Lys-Thr-Cys-Thr-NH₂;
Ac-D-hArg(CH₂CF₃)₂-D-hArg (CH₂CF₃)₂-Gly-Cys-Phe-D-Trp-Lys-Thr-Cys-Thr-NH₂;
Ac-D-hArg(CH₂CF₃)₂-D-hArg (CH₂CF₃)₂-Gly-Cys-Phe-D-Trp-Lys-Thr-Cys-Phe-NH₂;
Ac-D-hArg(Et)₂-D-hArg (Et)₂-Gly-Cys-Phe-D-Trp-Lys-Thr-Cys-Thr-NH₂;
Ac-Cys-Lys-Asn-4-Cl-Phe-Phe-D-Trp-Lys-Thr-Phe-Thr-Ser-D-Cys-NH₂;
Bmp-Tyr-D-Trp-Lys-Val-Cys-Thr-NH₂;
Bmp-Tyr-D-Trp-Lys-Val-Cys-Phe-NH₂;
Bmp-Tyr-D-Trp-Lys-Val-Cys-p-Cl-Phe-NH₂;
Bmp-Tyr-D-Trp-Lys-Val-Cys-β-Nal-NH₂;
H-D-β-Nal-Cys-Tyr-D-Trp-Lys-Val-Cys-Thr-NH₂;
H-D-Phe-Cys-Tyr-D-Trp-Lys-Abu-Cys-Thr-NH₂;
H-D-Phe-Cys-Tyr-D-Trp-Lys-Abu-Cys-β-Nal-NH₂;
H-pentafluoro-D-Phe-Cys-Tyr-D-Trp-Lys-Val-Cys-Thr-NH₂;
Ac-D-β-Nal-Cys-pentafluoro-Phe-D-Trp-Lys-Val-Cys-Thr-NH₂;
H-D-P-Nal-Cys-Tyr-D-Trp-Lys-Val-Cys-β-Nal-NH₂;
H-D-Phe-Cys-Tyr-D-Trp-Lys-Val-Cys-β-Nal-NH₂;
H-D-β-Nal-Cys-Tyr-D-Trp-Lys-Abu-Cys-Thr-NH₂;
H-D-p-Cl-Phe-Cys-Tyr-D-Trp-Lys-Abu-Cys-Thr-NH₂;
Ac-D-p-Cl-Phe-Cys-Tyr-D-Trp-Lys-Abu-Cys-Thr-NH₂;
H-D-Phe-Cys-β-Nal-D-Trp-Lys-Val-Cys-Thr-NH₂;
H-D-Phe-Cys-Tyr-D-Trp-Lys-Cys-Thr-NH₂;
cyclo (Pro-Phe-D-Trp-N-Me-Lys-Thr-Phe);
cyclo (Pro-Phe-D-Trp-N-Me-Lys-Thr-Phe);

cyclo (Pro-Phe-D-Trp-Lys-Thr-N-Me-Phe);
cyclo (N-Me-Ala-Tyr-D-Trp-Lys-Thr-Phe);
cyclo (Pro-Tyr-D-Trp-Lys-Thr-Phe);

tostatin agonist or a pharmaceutically acceptable salt thereof is D-β-Nal-Cys-Tyr-D-Trp-Lys-Thr-Cys-Thr-NH$_2$, H-Cys-Phe-Phe-D-Trp-Lys-Thr-Phe-Cys-NH$_2$,

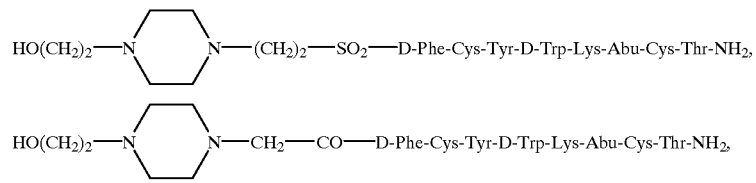

cyclo (Pro-Phe-D-Trp-Lys-Thr-Phe);
cyclo (Pro-Phe-L-Trp-Lys-Thr-Phe);
cyclo (Pro-Phe-D-Trp(F)-Lys-Thr-Phe);
cyclo (Pro-Phe-Trp(F)-Lys-Thr-Phe);
cyclo (Pro-Phe-D-Trp-Lys-Ser-Phe);
cyclo (Pro-Phe-D-Trp-Lys-Thr-p-Cl-Phe);
cyclo (D-Ala-N-Me-D-Phe-D-Thr-D-Lys-Trp-D-Phe);
cyclo (D-Ala-N-Me-D-Phe-D-Val-Lys-D-Trp-D-Phe);
cyclo (D-Ala-N-Me-D-Phe-D-Thr-Lys-D-Trp-D-Phe);
cyclo (D-Abu-N-Me-D-Phe-D-Val-Lys-D-Trp-D-Tyr);
cyclo (Pro-Tyr-D-Trp-t-4-AchxAla-Thr-Phe);
cyclo (Pro-Phe-D-Trp-t-4-AchxAla-Thr-Phe);
cyclo (N-Me-Ala-Tyr-D-Trp-Lys-Val-Phe);
cyclo (N-Me-Ala-Tyr-D-Trp-t-4-AchxAla-Thr-Phe);
cyclo (Pro-Tyr-D-Trp-4-Amphe-Thr-Phe);
cyclo (Pro-Phe-D-Trp-4-Amphe-Thr-Phe);
cyclo (N-Me-Ala-Tyr-D-Trp-4-Amphe-Thr-Phe);
cyclo (Asn-Phe-Phe-D-Trp-Lys-Thr-Phe-Gaba);
cyclo (Asn-Phe-Phe-D-Trp-Lys-Thr-Phe-Gaba-Gaba);
cyclo (Asn-Phe-D-Trp-Lys-Thr-Phe);
cyclo (Asn-Phe-Phe-D-Trp-Lys-Thr-Phe-NH(CH$_2$)$_4$CO);
cyclo (Asn-Phe-Phe-D-Trp-Lys-Thr-Phe-β-Ala);
cyclo (Asn-Phe-Phe-D-Trp-Lys-Thr-Phe-D-Glu)-OH;
cyclo (Phe-Phe-D-Trp-Lys-Thr-Phe);
cyclo (Phe-Phe-D-Trp-Lys-Thr-Phe-Gly);
cyclo (Phe-Phe-D-Trp-Lys-Thr-Phe-Gaba);
cyclo (Asn-Phe-Phe-D-Trp-Lys-Thr-Phe-Gly);
cyclo (Asn-Phe-Phe-D-Trp(F)-Lys-Thr-Phe-Gaba);
cyclo (Asn-Phe-Phe-D-Trp(NO$_2$)-Lys-Thr-Phe-Gaba);
cyclo (Asn-Phe-Phe-Trp(Br)-Lys-Thr-Phe-Gaba);
cyclo (Asn-Phe-Phe-D-Trp-Lys-Thr-Phe(I)-Gaba);
cyclo (Asn-Phe-Phe-D-Trp-Lys-Thr-Tyr(But)-Gaba);
cyclo (Bmp-Lys-Asn-Phe-Phe-D-Trp-Lys-Thr-Phe-Thr-Pro-Cys)-OH;
cyclo (Bmp-Lys-Asn-Phe-Phe-D-Trp-Lys-Thr-Phe-Thr-Pro-Cys)-OH;
cyclo (Bmp-Lys-Asn-Phe-Phe-D-Trp-Lys-Thr-Phe-Thr-Tpo-Cys)-OH;
cyclo (Bmp-Lys-Asn-Phe-Phe-D-Trp-Lys-Thr-Phe-Thr-MeLeu-Cys)-OH;
cyclo (Phe-Phe-D-Trp-Lys-Thr-Phe-Phe-Gaba);
cyclo (Phe-Phe-D-Trp-Lys-Thr-Phe-D-Phe-Gaba);
cyclo (Phe-Phe-D-Trp(5F)-Lys-Thr-Phe-Phe-Gaba);
cyclo (Asn-Phe-Phe-D-Trp-Lys(Ac)-Thr-Phe-NH-(CH$_2$)$_3$-CO);
cyclo (Lys-Phe-Phe-D-Trp-Lys-Thr-Phe-Gaba);
cyclo (Lys-Phe-Phe-D-Trp-Lys-Thr-Phe-Gaba); or
cyclo (Orn-Phe-Phe-D-Trp-Lys-Thr-Phe-Gaba) or a pharmaceutically acceptable salt thereof.

Also, this invention provides a method of inhibiting overexpression of TGF-β which comprises administering to a subject an effective amount of somatostatin agonist or a pharmaceutically acceptable salt thereof wherein the somaor D-Phe-cyclo(Cys-Phe-D-Trp-Lys-Thr-Cys)-Thr-ol or a pharmaceutically acceptable salt thereof. Each of the foregoing methods is preferred.

In still another aspect, this invention provides a method wherein it is preferred that of each of the methods described above that the somatostatin agonist is administered parenterally and more preferably that the somatostatin agonist administered parenterally is administered in a sustained release formulation. It is also preferred that of each of the methods described above that the somatostatin agonist or pharmaceutically acceptable salt thereof is administered orally or topically. Each of the foregoing methods is preferred.

Still another aspect of the present invention provides a pharmaceutical composition useful for inhibiting fibrosis in a patient which comprises a pharmaceutically acceptable carrier and an effective amount of somatostatin, somatostatin agonist or a pharmaceutically acceptable salt thereof, preferred of the immediately foregoing pharmaceutical composition is a pharmaceutical composition which comprises a somatostatin agonist or a pharmaceutically acceptable salt thereof.

Still another aspect of the present invention provides a pharmaceutical composition useful for inhibiting overexpression of TGF-β which comprises a pharmaceutically acceptable carrier and an effective amount of somatostatin, somatostatin agonist or a pharmaceutically acceptable salt thereof, preferred of the immediately foregoing pharmaceutical composition is a pharmaceutical composition which comprises a somatostatin agonist or a pharmaceutically acceptable salt thereof.

Definition of "somatostatin agonist" will be defined below. A therapeutically effective amount depends upon the condition being treated, treatment regimen, the route of administration chosen, and the specific activity of the compound used and ultimately will be decided by the attending physician or veterinarian. In one embodiment, the somatostatin agonist is administered to the patient until the fibrotic process is arrested and/or is reversed. In another embodiment, the somatostatin agonist is administered for the lifetime of the patient. In still another embodiment, the somatostatin agonist is administered prior to the event which initiates the fibrotic process (e.g., prior to chemotherapy or exposure to radiation such as in radiation therapy).

Somatostatin or a somatostatin agonist may be injected parenterally, e.g., intravenously, into the bloodstream of the subject being treated. However, it will be readily appreciated by those skilled in the art that the route, such as subcutaneous, intramuscular, intraperitoneal, enterally, transdermally, transmucously, sustained released polymer compositions (e.g., a lactic acid polymer or lactic-glycolic acid copolymer microparticle or implant), profusion, nasal, oral, topical, vaginal, rectal, nasal, sublingual, etc., will vary with the condition being treated and the activity and bioavailability of the somatostatin agonist being used.

The dosage of active ingredient administered in a method of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.000001 to 100 mg/kg of body weight daily are administered to humans and other animals, e.g., mammals.

A preferred dosage range is 0.01 to 5.0 mg/kg of body weight daily which can be administered as a single dose or divided into multiple doses.

While it is possible for the somatostatin agonist to be administered as the pure or substantially pure compound, it may also be presented as a pharmaceutical formulation or preparation. The formulations to be used in the present invention, for both humans and animals, comprise any of the somatostatin agonists to be described below, together with one or more pharmaceutically acceptable carriers thereof, and optionally other therapeutic ingredients.

The carrier must be "acceptable" in the sense of being compatible with the active ingredient(s) of the formulation (e.g., capable of stabilizing peptides) and not deleterious to the subject to be treated. Desirably, the formulation should not include oxidizing agents or other substances with which peptides are known to be incompatible. For example, somatostatin agonists in the cyclized form (e.g., internal cysteine disulfide bond) are oxidized; thus, the presence of reducing agents as excipients could lead to an opening of the cysteine disulfide bridge. On the other hand, highly oxidative conditions can lead to the formation of cysteine sulfoxide and to the oxidation of tryptophane. Consequently, it is important to carefully select the excipient. pH is another key factor, and it may be necessary to buffer the product under slightly acidic conditions (pH 5 to 6).

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient with finely divided solid carriers, and then, if necessary, as in the case of tablets, forming the product into the desired shape and size.

Formulations suitable for parenteral (e.g., intravenous) administration, on the other hand, conveniently comprise sterile aqueous solutions of the active ingredient(s). Preferably, the solutions are isotonic with the blood of the subject to be treated. Such formulations may be conveniently prepared by dissolving active ingredient(s) in a solvent comprising water to produce an aqueous solution, and rendering said solution sterile. The formulation may be presented in unit or multi-dose containers, for example, sealed ampoules or vials.

Formulations suitable for sustained release parenteral administrations (e.g., biodegradable polymer formulations) are also well known in the art. See, e.g., U.S. Pat. Nos. 3,773,919 and 4,767,628, the teachings of which are incorporated herein by reference, and PCT Publication No. WO 94/15587.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

For topical administration, they are best used in the form of solutions, creams, salves, lotions, ointments and the like.

The somatostatin or somatostatin agonist may also be administered with known initiators (e.g., chemotherapeutics) of the fibrotic process to ameliorate fibrosis or to prevent the initiation of fibrosis.

Other features and advantages of the invention will be apparent from the following description of the preferred embodiments and from the claims.

Abbreviations

β-Nal=β-naphthylalanine
β-Pal=β-pyridylalanine
hArg(Bu)=N-guanidino-(butyl)-homoarginine
hArg(Et)$_2$=N,N'-guanidino-(diethyl)-homoarginine
hArg(CH$_2$CF$_3$)$_2$=N,N'-guanidino-bis-(2,2,2,-trifluoroethyl)-homoarginine
hArg(CH$_3$, hexyl)=N,N'-guanidino-(methyl, hexyl)-homoarginine
Lys(Me)=N$^\epsilon$-methyllysine
Lys(iPr)=N$^\epsilon$-isopropyllysine
AmPhe=aminomethylphenylalanine
AChxAla=aminocyclohexylalanine
Abu=α-aminobutyric acid
Tpo=4-thiaproline
MeLeu=N-methylleucine
Orn=ornithine
Nle=norleucine
Nva=norvaline
Trp(Br)=5-bromo-tryptophan
Trp(F)=5-fluoro-tryptophan
Trp(NO$_2$)=5-nitro-tryptophan
Gaba=γ-aminobutyric acid
Bmp=β-mercaptopropionyl
Ac=acetyl
Pen=pencillamine.

DETAILED DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

The fibrosis which is inhibited can be located in various parts of the body and can be of a particular kind, for example, the fibrosis may be located:

in the kidney, for example, fibrosis as observed in glomerulonenephritis (see Yoshioka et al., Lab Invest 1993;68: 154–63), diabetic nephropathy (see Yamamoto et al., Proc Natl Acad Sci USA 1993;90: 1814–8), allograft rejection (see Shihab et al., J Am Soc Nephrol 1993;4: 671, abstract), and HIV nephropathy (see Border et al., J Am Soc Nephrol 1993;4: 675, abstract);

in the liver, for example, cirrhosis (see Castilla et al., N Engl J Med 1991;324: 933–940 and Nagy et al., Hepatology 1991;14: 269–73), and veno-occlusive disease (see Anscher et al., N Engl J Med 1993;328: 1592–8);

in the lung, for example, idiopathic fibrosis (see Anscher et al., N Engl J Med 1993;328: 1592–8 and Brockelmann et al., Proc Natl Acad Sci USA 1991;88: 6642–6) and autoimmune fibrosis (see Deguchi, Ann Rheum Dis 1992;51: 362–5);

in the skin, for example, systemic sclerosis (see Kulozik et al., J Clin Invest 1990;86: 917–22), keloids (see Peltonen et al., J Invest Dermatol 1991;97: 240–8), scars (see Ghahary et al., J Lab Clin Med 1993;122: 465–73), and eosinophilia-myalgia syndrome (see Varga et al., Ann Intern Med 1992;116: 140–7);

in the central nervous system, for example, intraocular fibrosis (see Conner et al., J Clin Invest 1989;83: 1661–6);

in the cardiovascular system, for example, vascular restenosis (see Nikol et al., J Clin Invest 1992;90: 1582–92);

in the nose, for example, nasal polyposis (see Ohno et al., J Clin Invest 1992;89: 1662–8);

in bone or bone marrow (see Harrison's Principles of Internal Medicine, Thirteenth Edition, Volume 2, Chapter 362, pp. 2197–2199; Najean, Y. et al., Leuk Lymphoma, 1996, 22 Suppl 1:111–119; and Reith, J. D. et al., Am J Srg Pathol, 1996 20(11): 1368–1377);

in an endocrine organ (see Endocrinology, Third Edition, Edited by Leslie J. DeGroot, Vol. 1, pp. 165–177 and pp. 747–751);

and in the gastrointestinal system (see Mizoi, T. et al, Cancer Res., 1993 53(1): 183–190; and Tahara, E., J. Cancer Res. Clin. Oncol., 1990, 116(2), 121–131).

A fibrotic disorder may be induced by a number of causes including:

chemotherapy, for example, pulmonary fibrosis resulting from bleomycin, chlorambucil, cyclophsphamide, methotrexate, mustine, or procarbazine treatment (see Key Facts in Oncology by Lilly, Drug Therapy, p.11, 1994);

radiation exposure whether accidental or purposeful as in radiation therapy, for example, interstitial lung disease (ILD) resulting from radiation (see Cecil Textbook of Medicine, 19$^{th}$ Edition, edited by James B. Wyngaarden, Lloyd H. Smith, Jr., and J. Claude Bennet, Chapter 60, Table 60–5, p. 399, 1992);

environmental or industrial factors or pollutants such as chemicals, fumes, metals, vapors, gases, etc., for example, ILD resulting from asbestos or coal dust (see Cecil Textbook of Medicine, 19$^{th}$ Edition, edited by James B. Wyngaarden, Lloyd H. Smith, Jr., and J. Claude Bennet, Chapter 60, Table 60–2, p. 398, 1992);

a drug or a combination of drugs, for example, antibiotics (e.g. penicillins, sulfonamides, etc.), cardiovascular drugs (e.g. hydralazine, beta blockers, etc.), CNS drugs (phenytoin, chlorpromazine, etc.) anti-inflammatory drugs (e.g. gold salts, phenylbutazone, etc.), etc. can cause ILD (see Cecil Textbook of Medicine, 19$^{th}$ Edition, edited by James B. Wyngaarden, Lloyd H. Smith, Jr., and J. Claude Bennet, Chapter 60, Table 60–4, p. 398, 1992);

an immune reaction disorder, for example, chronic graft-vs-host disease with dermal fibrosis, (see Fibrotic Skin Diseases, Editorial, J. Uitto and S. Jimenez, Arch, Dermatol, Vol 126, May 1990, p.662);

disease states such as aspiration pneumonia which is a known cause of ILD, (see Harrison's Principles of Internal Medicine, Twelfth Edition, Chapter 211, Table 211–1, P 1083) and parasite induced fibrosis (see Wahl, S. M., Kidney Int, 1997, 51(5): 1370–1375); and wounds, for example, blunt trauma, surgical incisions, battlefield wounds, etc., as in penetrating injuries of the CNS (see Ann Logan, et al., Brain Research, 587 (1992), 216–225).

Somatostatin and its Agonists

Somatostatin (somatotropin release inhibiting factor or SRIF) has both a 14 amino acid isoform (somatostatin-14) and a 28 amino acid isoform (somatostatin-28). See Wilson, J. & Foster, D., *Williams Textbook of Endocrinology*, p. 510 (7th ed., 1985). The compound is an inhibitor of secretion of the growth hormone and was originally isolated from the hypothalamus. Brazeau et al., Science 179:77 (1973). Native somatostatin has a very short duration of effect in vivo since it is rapidly inactivated by endo- and exopeptidase. Many novel analogs have been prepared in order to enhance the duration of effect, biological activity, and selectivity (e.g., for the particular somatostatin receptor) of this hormone. Such analogs will be called "somatostatin agonists" herein. Further, compounds that are short peptides modified by organic moieties and non-peptides, such as organic molecules that do not have an art-recognized amino acid as part of its structure, that bind to somatostatin receptor(s) are also within the meaning of "somatostatin agonists".

Various somatostatin receptors (SSTRs) have been isolated, e.g., SSTR-1, SSTR-2, SSTR-3, SSTR-4, and SSTR-5. Thus, the somatostatin agonist may be a SSTR-1 agonist, SSTR-2 agonist, SSTR-3 agonist, SSTR-4 agonist of a SSTR-5 agonist. In one embodiment, the somatostatin agonist is an SSTR-2 agonist or an SSTR-5 agonist. What is meant by an "SSTR-2 agonist" or an "SSTR-5 agonist" is a compound which (1) has a high affinity (e.g., Ki of less than 1 :M or, preferably, of less than 10 nM) for the SSTR-2 or SSTR-5, respectively (as defined by the receptor binding assay described below), and (2) inhibits the formation of fibrosis (e.g., as defined by the biological assay described below). The somatostatin agonist may also be selective for a particular somatostatin receptor, e.g., have a higher binding affinity for a particular somatostatin receptor subtype. In one embodiment, the somatostatin receptor is an SSTR-2 or SSTR-5 selective agonist.

Somatostatin agonists which can be used to practice the therapeutic method of the present invention include, but are not limited to, those covered by formulae or those specifically recited in the publications set forth below, all of which are hereby incorporated by reference.

EP Application No. P5 164 EU (Inventor: G. Keri);

Van Binst, G. et al. Peptide Research 5:8 (1992);

Horvath, A. et al. Abstract, "Conformations of Somatostatin Analogs Having Antitumor Activity", 22nd European peptide Symposium, September 13–19, 1992, Interlaken, Switzerland;

PCT Application WO 91/09056 (1991);
EP Application 0 363 589 A2 (1990);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987);
U.S. Pat. No. 4,650,787 (1987);
U.S. Pat. No. 4,603,120 (1986);
U.S. Pat. No. 4,585,755 (1986);
EP Application 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);

-continued

U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,190 (1980);
U.S. Pat. No. 4,211,693 (1980);
U.S. Pat. No. 4,190,648 (1980);
U.S. Pat. No. 4,146,612 (1979); and
U.S. Pat. No. 4,133,782 (1979).

Examples of somatostatin agonists include, but are not limited to, the following somatostatin analogs and pharmaceutically acceptable salt thereof which are disclosed in the above-cited references:

D-β-Nal-Cys-Tyr-D-Trp-Lys-Thr-Cys-Thr-$NH_2$ (BIM-23014);

D-Phe-Cys-Phe-D-Trp-Lys-Thr-Cys-β-Nal-$NH_2$;

D-Phe-Cys-Tyr-D-Trp-Lys-Thr-Cys-β-Nal-$NH_2$;

D-β-Nal-Cys-Phe-D-Trp-Lys-Thr-Cys-Thr-$NH_2$;

D-Phe-Cys-Tyr-D-Trp-Lys-Thr-Pen-Thr-$NH_2$;

D-Phe-Cys-Phe-D-Trp-Lys-Thr-Pen-Thr-$NH_2$;

D-Phe-Cys-Tyr-D-Trp-Lys-Thr-Pen-Thr-OH;

D-Phe-Cys-Phe-D-Trp-Lys-Thr-Pen-Thr-OH;

Gly-Pen-Phe-D-Trp-Lys-Thr-Cys-Thr-OH;

Phe-Pen-Tyr-D-Trp-Lys-Thr-Cys-Thr-OH;

Phe-Pen-Phe-D-Trp-Lys-Thr-Pen-Thr-OH;

H-D-Phe-Cys-Phe-D-Trp-Lys-Thr-Cys-Thr-ol;

H-D-Phe-Cys-Phe-D-Trp-Lys-Thr-Cys-Thr-$NH_2$;

H-D-Trp-Cys-Tyr-D-Trp-Lys-Val-Cys-Thr-$NH_2$;

H-D-Trp-Cys-Phe-D-Trp-Lys-Thr-Cys-Thr-$NH_2$;

H-D-Phe-Cys-Tyr-D-Trp-Lys-Val-Cys-Thr-$NH_2$;

H-D-Phe-Cys-Tyr-D-Trp-Lys-Val-Cys-Trp-$NH_2$;

H-D-Phe-Cys-Tyr-D-Trp-Lys-Val-Cys-Thr-$NH_2$;

Ac-D-Phe-Lys*-Tyr-D-Trp-Lys-Val-Asp-Thr-$NH_2$ (an amide bridge formed between Lys* and Asp);

Ac-hArg $(Et)_2$-Gly-Cys-Phe-D-Trp-Lys-Thr-Cys-Thr-$NH_2$;

Ac-D-hArg $(Et)_2$-Gly-Cys-Phe-D-Trp-Lys-Thr-Cys-Thr-$NH_2$;

Ac-D-hArg(Bu)-Gly-Cys-Phe-D-Trp-Lys-Thr-Cys-Thr-$NH_2$;

Ac-D-hArg $(Et)_2$-CYS-Phe-D-Trp-Lys-Thr-Cys-Thr-$NH_2$;

Ac-L-hArg $(Et)_2$-Cys-Phe-D-Trp-Lys-Thr-Cys-Thr-$NH_2$;

Ac-D-hArg $(CH_2CF_3)_2$-Cys-Phe-D-Trp-Lys-Thr-Cys-Thr-$NH_2$;

Ac-D-hArg $(CH_2CF_3)_2$-Gly-Cys-Phe-D-Trp-Lys-Thr-Cys-Thr-$NH_2$;

Ac-D-hArg $(CH_2CF_3)_2$-Gly-Cys-Phe-D-Trp-Lys-Thr-Cys-Phe-$H_2$;

Ac-D-hArg $(CH_2CF_3)_2$-Gly-Cys-Phe-D-Trp-Lys-Thr-Cys-Thr-NHEt;

Ac-L-hArg $(CH_2CF_3)_2$-Gly-Cys-Phe-D-Trp-Lys-Thr-Cys-Thr-$NH_2$;

Ac-D-hArg $(CH_2CF_3)_2$-Gly-Cys-Phe-D-Trp-Lys (Me)-Thr-Cys-Thr-$NH_2$;

Ac-D-hArg $(CH_2CF_3)_2$-Gly-Cys-Phe-D-Trp-Lys (Me)-Thr-Cys-Thr-NHEt;

Ac-hArg ($CH_3$, hexyl)-Gly-Cys-Phe-D-Trp-Lys-Thr-Cys-Thr-$NH_2$;

H-hArg (hexyl)$_2$-Gly-Cys-Phe-D-Trp-Lys-Thr-Cys-Thr-$NH_2$;

Ac-D-hArg $(Et)_2$-Gly-Cys-Phe-D-Trp-Lys-Thr-Cys-Thr-NHEt;

Ac-D-hArg $(Et)_2$-Gly-Cys-Phe-D-Trp-Lys-Thr-Cys-Phe-$NH_2$;

Propionyl-D-hArg $(Et)_2$-Gly-Cys-Phe-D-Trp-Lys(iPr)-Thr-Cys-Thr-$NH_2$;

Ac-D-β-Nal-Gly-Cys-Phe-D-Trp-Lys-Thr-Cys-Gly-hArg $(Et)_2$-$NH_2$;

Ac-D-Lys(iPr)-Gly-Cys-Phe-D-Trp-Lys-Thr-Cys-Thr-$NH_2$;

Ac-D-hArg $(CH_2CF_3)_2$-D-hArg $(CH_2CF_3)_2$-Gly-Cys-Phe-D-Trp-Lys-Thr-Cys-Thr-$NH_2$;

Ac-D-hArg $(CH_2CF_3)_2$-D-hArg $(CH_2CF_3)_2$-Gly-Cys-Phe-D-Trp-Lys-Thr-Cys-Phe-$NH_2$;

Ac-D-hArg$(Et)_2$-D-hArg$(Et)_2$-Gly-Cys-Phe-D-Trp-Lys-Thr-Cys-Thr-$NH_2$;

Ac-Cys-Lys-Asn-4-Cl-Phe-Phe-D-Trp-Lys-Thr-Phe-Thr-Ser-D-Cys-$NH_2$;

Bmp-Tyr-D-Trp-Lys-Val-Cys-Thr-$NH_2$;

Bmp-Tyr-D-Trp-Lys-Val-Cys-Phe-$NH_2$;

Bmp-Tyr-D-Trp-Lys-Val-Cys-p-Cl-Phe-$NH_2$;

Bmp-Tyr-D-Trp-Lys-Val-Cys-β-Nal-$NH_2$;

H-D-β-Nal-Cys-Tyr-D-Trp-Lys-Val-Cys-Thr-$NH_2$;

H-D-Phe-Cys-Tyr-D-Trp-Lys-Abu-Cys-Thr-$NH_2$;

H-D-Phe-Cys-Tyr-D-Trp-Lys-Abu-Cys-β-Nal-$NH_2$;

H-pentafluoro-D-Phe-Cys-Tyr-D-Trp-Lys-Val-Cys-Thr-$NH_2$;

Ac-D-β-Nal-Cys-pentafluoro-Phe-D-Trp-Lys-Val-Cys-Thr-$NH_2$;

H-D-β-Nal-Cys-Tyr-D-Trp-Lys-Val-Cys-β-Nal-$NH_2$;

H-D-Phe-Cys-Tyr-D-Trp-Lys-Val-Cys-β-Nal-$NH_2$;

H-D-β-Nal-Cys-Tyr-D-Trp-Lys-Abu-Cys-Thr-$NH_2$;

H-D-p-Cl-Phe-Cys-Tyr-D-Trp-Lys-Abu-Cys-Thr-$NH_2$;

Ac-D-p-Cl-Phe-Cys-Tyr-D-Trp-Lys-Abu-Cys-Thr-$NH_2$;

H-D-Phe-Cys-β-Nal-D-Trp-Lys-Val-Cys-Thr-$NH_2$;

H-D-Phe-Cys-Tyr-D-Trp-Lys-Cys-Thr-$NH_2$;

cyclo (Pro-Phe-D-Trp-N-Me-Lys-Thr-Phe);

cyclo (Pro-Phe-D-Trp-N-Me-Lys-Thr-Phe);

cyclo (Pro-Phe-D-Trp-Lys-Thr-N-Me-Phe);

cyclo (N-Me-Ala-Tyr-D-Trp-Lys-Thr-Phe);

cyclo (Pro-Tyr-D-Trp-Lys-Thr-Phe)

cyclo (Pro-Phe-D-Trp-Lys-Thr-Phe);

cyclo (Pro-Phe-L-Trp-Lys-Thr-Phe);

cyclo (Pro-Phe-D-Trp(F)-Lys-Thr-Phe);

cyclo (Pro-Phe-Trp(F)-Lys-Thr-Phe);

cyclo (Pro-Phe-D-Trp-Lys-Ser-Phe);

cyclo (Pro-Phe-D-Trp-Lys-Thr-p-Cl-Phe);

cyclo (D-Ala-N-Me-D-Phe-D-Thr-D-Lys-Trp-D-Phe);

cyclo (D-Ala-N-Me-D-Phe-D-Val-Lys-D-Trp-D-Phe);

cyclo (D-Ala-N-Me-D-Phe-D-Thr-Lys-D-Trp-D-Phe);

cyclo (D-Abu-N-Me-D-Phe-D-Val-Lys-D-Trp-D-Tyr);

cyclo (Pro-Tyr-D-Trp-t-4-AchxAla-Thr-Phe);

cyclo (Pro-Phe-D-Trp-t-4-AchxAla-Thr-Phe);

cyclo (N-Me-Ala-Tyr-D-Trp-Lys-Val-Phe);

cyclo (N-Me-Ala-Tyr-D-Trp-t-4-AchxAla-Thr-Phe);

cyclo (Pro-Tyr-D-Trp-4-Amphe-Thr-Phe);
cyclo (Pro-Phe-D-Trp-4-Amphe-Thr-Phe);
cyclo (N-Me-Ala-Tyr-D-Trp-4-Amphe-Thr-Phe);
cyclo (Asn-Phe-Phe-D-Trp-Lys-Thr-Phe-Gaba);
cyclo (Asn-Phe-Phe-D-Trp-Lys-Thr-Phe-Gaba-Gaba);
cyclo (Asn-Phe-D-Trp-Lys-Thr-Phe);
cyclo (Asn-Phe-Phe-D-Trp-Lys-Thr-Phe-NH (CH$_2$)$_4$CO);
cyclo (Asn-Phe-Phe-D-Trp-Lys-Thr-Phe-β-Ala);
cyclo (Asn-Phe-Phe-D-Trp-Lys-Thr-Phe-D-Glu)-OH;
cyclo (Phe-Phe-D-Trp-Lys-Thr-Phe);
cyclo (Phe-Phe-D-Trp-Lys-Thr-Phe-Gly);
cyclo (Phe-Phe-D-Trp-Lys-Thr-Phe-Gaba);
cyclo (Asn-Phe-Phe-D-Trp-Lys-Thr-Phe-Gly);
cyclo (Asn-Phe-Phe-D-Trp(F)-Lys-Thr-Phe-Gaba);
cyclo (Asn-Phe-Phe-D-Trp (NO$_2$) -Lys-Thr-Phe-Gaba);
cyclo (Asn-Phe-Phe-Trp(Br)-Lys-Thr-Phe-Gaba);
cyclo (Asn-Phe-Phe-D-Trp-Lys-Thr-Phe(I)-Gaba);
cyclo (Asn-Phe-Phe-D-Trp-Lys-Thr-Tyr(But)-Gaba);
cyclo (Bmp-Lys-Asn-Phe-Phe-D-Trp-Lys-Thr-Phe-Thr-Pro-Cys)-OH;
cyclo (Bmp-Lys-Asn-Phe-Phe-D-Trp-Lys-Thr-Phe-Thr-Pro-Cys)-OH;
cyclo (Bmp-Lys-Asn-Phe-Phe-D-Trp-Lys-Thr-Phe-Thr-Tpo-Cys)-OH;
cyclo (Bmp-Lys-Asn-Phe-Phe-D-Trp-Lys-Thr-Phe-Thr-MeLeu-Cys)-OH;
cyclo (Phe-Phe-D-Trp-Lys-Thr-Phe-Phe-Gaba);
cyclo (Phe-Phe-D-Trp-Lys-Thr-Phe-D-Phe-Gaba);
cyclo (Phe-Phe-D-Trp(5F)-Lys-Thr-Phe-Phe-Gaba);
cyclo (Asn-Phe-Phe-D-Trp-Lys (Ac)-Thr-Phe-NH- (CH$_2$)$_3$-CO);
cyclo (Lys-Phe-Phe-D-Trp-Lys-Thr-Phe-Gaba);
cyclo (Lys-Phe-Phe-D-Trp-Lys-Thr-Phe-Gaba);
cyclo (Orn-Phe-Phe-D-Trp-Lys-Thr-Phe-Gaba); and
H-Cys-Phe-Phe-D-Trp-Lys-Thr-Phe-Cys-NH2(BIM-23268).

Note that for all somatostatin agonists described herein, each amino acid residue represents the structure of —NH—C(R)H—CO—, in which R is the side chain (e.g., CH$_3$ for Ala) except for Thr-ol which means —NH—CH(CH(CH$_3$)OH)—CH$_2$—OH and Pro which means prolinyl. Lines between amino acid residues represent peptide bonds which join the amino acids.

Also, where the amino acid residue is optically active, it is the L-form configuration that is intended unless D-form is expressly designated. A disulfide bridge is formed between two Cys residues; however, it is not shown.

Use of linear somatostatin agonists of the following formula is also within the invention:

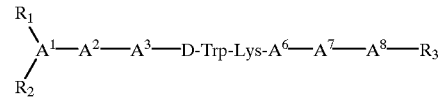

or a pharmaceutically acceptable salt thereof, wherein
$A^1$ is a D- or L- isomer of Ala, Leu, Ile, Val, Nle, Thr, Ser, β-Nal, β-Pal, Trp, Phe, 2,4-dichioro-Phe, pentafluoro-Phe, p-X-Phe, or o-X-Phe;
$A^2$ is Ala, Leu, Ile, Val, Nle, Phe, β-Nal, pyridyl-Ala, Trp, 2,4-dichloro-Phe, pentafluoro-Phe, o-X-Phe, or p-X-Phe;
$A^3$ is pyridyl-Ala, Trp, Phe, β-Nal, 2,4-dichloro-Phe, pentafluoro-Phe, o-X-Phe, or p-X-Phe;
$A^6$ is Val, Ala, Leu, Ile, Nle, Thr, Abu, or Ser;
$A^7$ is Ala, Leu, Ile, Val, Nle, Phe, β-Nal, pyridyl-Ala, Trp, 2,4-dichloro-Phe, pentafluoro-Phe, o-X-Phe, or p-X-Phe;
$A^8$ is a D- or L-isomer of Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe;
each $R_1$ and $R_2$, independently, is H, lower acyl or lower alkyl; and $R_3$ is OH or NH$_2$; provided that at least one of $A^1$ and $A^8$ and one of $A^2$ and $A^7$ must be an aromatic amino acid; and further provided that $A^1$ $A^2$, $A^7$ and $A^8$ cannot all be aromatic amino acids.

Examples of linear agonists to be used in the method of this invention include:
H-D-Phe-p-chloro-Phe-Tyr-D-Trp-Lys-Thr-Phe-Thr-NH$_2$;
H-D-Phe-p-NO$_2$-Phe-Tyr-D-Trp-Lys-Val-Phe-Thr-NH$_2$;
H-D-Nal-p-chloro-Phe-Tyr-D-Trp-Lys-Val-Phe-Thr-NH$_2$;
H-D-Phe-Phe-Phe-D-Trp-Lys-Thr-Phe-Thr-NH$_2$;
H-D-Phe-Phe-Tyr-D-Trp-Lys-Val-Phe-Thr-NH$_2$;
H-D-Phe-p-chloro-Phe-Tyr-D-Trp-Lys-Val-Phe-Thr-NH$_2$; and
H-D-Phe-Ala-Tyr-D-Trp-Lys-Val-Ala-β-D-Nal-NH$_2$ or a pharmaceutically acceptable salt thereof.

If desired, one or more chemical moieties, e.g., a sugar derivative, mono- or poly-hydroxy C$_{2-12}$ alkyl, mono or polyhydroxy C$_{2-12}$ acyl groups, or a piperazine derivative, can be attached to the somatostatin agonist, e.g., to the N-terminus amino acid. See PCT Application WO 88/02756, European Application 0 329 295, and PCT Application No. Wo 94/04752. An example of a somatostatin agonists which contain N-terminal chemical substitutions are:

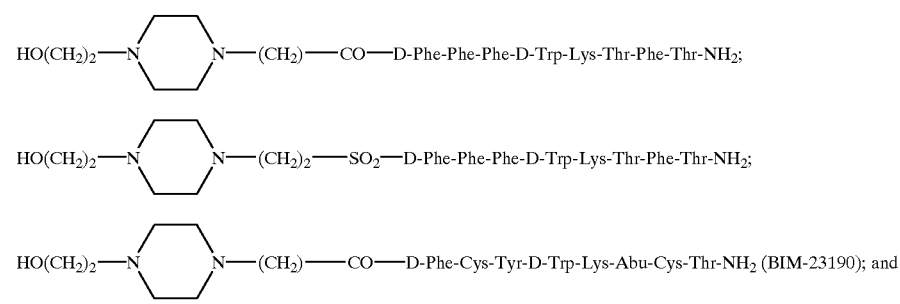

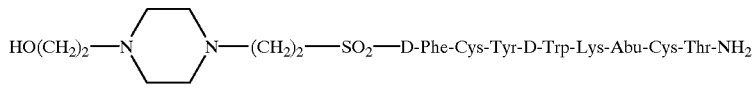

(BIM-23197) or a pharmaceutically acceptable salt thereof.

Synthesis of somatostatin agonists

The methods for synthesizing somatostatin agonists are well documented and are within the ability of a person of ordinary skill in the art, for example, as illustrated in the U.S. Patents and other references cited hereinabove.

Synthesis of short amino acid sequences is well established in the peptide art. For example, synthesis of D-Nal-Cys-Tyr-D-Trp-Lys-Val-Cys-Thr-NH$_2$, described above, can be synthesized by following the protocol set forth in U.S. Pat. No. 4,853,371 and synthesis of H-D-Phe-Phe-Phe-D-Trp-Lys-Thr-Phe-Thr-NH$_2$, described above, can be achieved by following the protocol set forth in Example I of European Patent Application 0 395 417 Al. The synthesis of somatostatin agonists with a substituted N-terminus can be achieved, for example, by following the protocol set forth in WO 88/02756, European Patent Application No. 0 329 295, and PCT Publication No. WO 94/04752.

Somatostatin Receptor Binding Assays

The human SSTR-1, SSTR-2, SSTR-3, SSTR-4, and SSTR-5 cDNA clones have been described (SSTR-1 and SSTR-2 in Yamada, Y., et al., Proc. Natl. Acad. Sci. USA., 89:251–255 (1992); SSTR-3 in Yamada, et al., Mol. Endocrinol. 6:2136–2142 (1993); and SSTR-4 and SSTR-5 in Yamada, et al., Biochem. Biophys. Res. Commun. 195:844–852 (1993)) and are also available from American Type Culture Collection (ATCC, Rockville, Md.) (ATCC Nos. 79044 (SSTR-1), 79046 (SSTR-2), and 79048 (SSTR-3)). Based on the restriction endonuclease maps, the entire coding region of each SSTR cDNA may be excised by suitable restriction endonuclease digestion (Maniatis, T., et al., *Molecular Cloning—A Laboratory Manual*, CSHL, 1982). Restriction endonucleases are available from New England Biolabs (Beverly, Mass.). This cDNA fragment was inserted into the mammalian expression vector, pCMV (Russell, D., et al., J. Biol. Chem., 264:8222–8229 (1989)), using standard molecular biology techniques (see e.g., Maniatis, T., et al., Molecular Cloning,-A Laboratory Manual, Cold Spring Harbor Laboratory, 1982) to produce the expression plasmid, pCMV-human SSTR-1 through pCMV-human SSTR-5. Other mammalian expression vectors include pcDNAl/Amp (Invitrogen, Sandlesy, Calif.). The expression plasmids were introduced into the suitable bacterial host, *E. Coli* HB101 (Stratagene, La Jolla, Calif.) and plasmid DNAs, for transfection, were prepared on Cesium Chloride gradients.

CHO-K1 (ovary, Chinese hamster) cells were obtained from ATCC (ATCC No. CCL 61). The cells were grown and maintained in Ham's F12 media (Gibco BRL, Grand Island, N.Y.) supplemented with 10% fetal bovine serum under standard tissue culture conditions. For transfection, the cells were seeded at a density 1×10$^6$/60-cm plate (Baxter Scientific Products, McGaw Park, Ill.). DNA mediated transfection was carried out using the calcium phosphate co-precipitation method (Ausubel, F. M., et al., Current Protocols in Molecular Biology, John Wiley & Sons, 1987). The plasmid pRSV-neo (ATCC; ATCC No. 37198) was included as a selectable marker at 1/10 the concentration of the expression plasmid. CHO-K1 clonal cell lines that have stably inherited the transfected DNA were selected for growth in Ham's F12 media containing 10% fetal bovine serum and 0.5 mg/ml of G418 (Sigma). The cells were ring-cloned and expanded in the same media for analysis.

Expression of the human SSTR-1 through SSTR-5 receptors in the CHO-K1 cells were detected by Northern blot analysis of total RNA prepared from the cells (Sambrook, J. E., et al., Molecular Cloning—A Laboratory Manual, Ed. 2., Cold Spring Harbor Laboratory, Cold Spring Harbor, N.Y., 1989) and by receptor binding using [$^{125}$I-Tyr$^{11}$] somatostatin-14 as a ligand. Transfected cell lines expressing the human SSTR receptors were clonally expanded in culture and used in the following SSTR binding protocol.

Crude membranes were prepared by homogenization of the transfected cells in 20 ml of ice-cold 50 mM Tris-HCl with a tissue homogenizer (setting 6, 15 sec) . Buffer was added to obtain a final volume of 40 ml, and the homogenate was centrifuged in a Sorval® SS-34 rotor (Sorval, Newtown, Conn.) at 39,000 g for 10 min at 0–4° C. The resulting supernatant was decanted and discarded. The pellet was rehomogenized in ice-cold buffer, diluted, and centrifuged as before. The final pellet was resuspended in the 10 mM Tris HCl and held on ice for the receptor binding assay.

Aliquots of the membrane preparation were incubated for 30 min at 30° C. with 0.05 nM [$^{125}$I-Tyr$^{11}$]somatostatin-14 (2000 Ci/mmol; Amersham Corp., Arlington Heights, Ill.) in 50 mM HEPES (pH 7.4) containing a test somatostatin agonist of various concentrations (e.g., $10^{-11}$ to $10^{-6}$), 10 mg/ml bovine serum albumin (fraction V) (Sigma Chemical Co., St. Louis, Mo.), MgCl$_2$ (5 mM), Trasylol (also known as aprotinin) (Sigma Chemical Co.) (200 KIU ml), bacitracin (Sigma Chemical Co.) (0.02 mg/ml), and phenylmethylsulphonyl fluoride (Sigma Chemical Co.) (0.02 mg/ml). The final assay volume was 0.3 ml. The incubations were terminated by rapid filtration through GF/C filters (presoaked in 0.3% polyethylenimine for 30 min) using a Brandel filtration manifold (Brandel Research and Development Co., Gaithersburg, Md.). Each tube and filter were then washed three times with 5 ml aliquots of ice-cold buffer. Specific binding was defined as the total [$^{125}$I-Tyr$^{11}$] somatostatin-14 bound minus that bound in the presence of 1000 nM of somatostatin-14. The Ki values for the tested somatostatin agonists were calculated by using the following formula: Ki=IC$_{50}$, /[1+(LC/LEC)] where IC$_{50}$ is the concentration of test somatostatin agonist required to inhibit 50 percent of the specific binding of the radioligand [$^{125}$I-Tyr$^{11}$] somatostatin-14, LC is the concentration of the radioligand (0.05 nM), and LEC is the equilibrium dissociation constant of the radioligand (0.16 nM) . The Ki values (nM) for the tested somatostatin agonists are shown in Table I.

TABLE I

|  | hSSTR-1 | hSSTR-2 | hSSTR-3 | hSSTR-4 | hSSTR-5 |
| --- | --- | --- | --- | --- | --- |
| Somatostatin-14 | 2.256 | 0.71 | 1.432 | 1.768 | 0.883 |
| Somatostatin-28 | 2.382 | 0.57 | 1.021 | 7.93 | 0.383 |
| BIM-23014 | 2414 | 1.10 | 121 | 1826 | 5.21 |
| BIM-23190 | 5210 | 0.47 | 2154 | 7537 | 11.1 |

TABLE I-continued

|  | hSSTR-1 | hSSTR-2 | hSSTR-3 | hSSTR-4 | hSSTR-5 |
|---|---|---|---|---|---|
| BIM-23197 | 6016 | 0.09 | 26.8 | 3897 | 9.81 |
| BIM-23268 | 12.27 | 6.84 | 62 | 19.96 | 0.38 |

Inhibition of Fibrosis

The somatostatin agonists may be tested for their ability to inhibit fibrosis.

(a) Demonstration of Anti-Fibrotic Activity In Vitro

Rats are injected either with anti-thymocyte serum (ATS) (see S. Okuda et al., J. Clin. Invest., Vol. 86, 1990, pp. 453–462) to induce glomerulonephritis or with phosphate buffered saline (PBS) to serve as controls. Six days later, the kidneys are removed, and the glomeruli are isolated and placed in culture for 72 hours. Culture conditions consist of 2000 glomeruli/well in a 1 ml volume of serum-free RPMI 1640 (with insulin supplementation) (Gibco, Gaithersburg, Md.). Test somatostatin or somatostatin agonists are added at the time of culture. The supernatant from the cultures is collected and stored at −70° C. until assayed to determine the concentration of collagen I, transforming growth factor β-1 (TGFβ-1), fibronectin containing an extra domain A (fibronectin EDA+), and plasminogen activator inhibitor I (PAI-I) as markers of fibrotic activity. In addition, individual glomeruli are examined by immunofluorescent staining and scored for relevant matrix proteins. Values were compared between PBS-treated, negative fibrotic control glomeruli; ATS-treated, non-drug treated, positive fibrotic control glomeruli; and the ATS-treated, drug treated, fibrotic glomeruli to determine the degree to which the fibrotic process is inhibited by somatostatin or the somatostatin agonists.

(b) Demonstration of Anti-Fibrotic Activity In Vivo

Rats are injected either with anti- hymocyte serum (ATS) to induce glomerulonephritis or with phosphate buffered saline (PBS) as a control. One hour later, treatment is initiated with somatostatin or a somatostatin agonist. Somatostatin or the somatostatin agonist are administered subcutaneously twice per day for 5 days. On day 5 the rats are placed in metabolic cages, and 24 hour urine is collected to determine protein content. On day 6, the kidneys are removed, and tissue samples are either placed in formalin or frozen for histological evaluation. Glomeruli are isolated from the remaining tissue and are placed in culture for 72 hours. Culture conditions consisted of 2000 glomeruli/well in a 1 ml volume of serum free RPMI 1640 (with insulin supplementation). The supernatant from the cultures are collected and stored at −70° C. until assayed to determine the concentration of collagen I, transforming growth factor β-1 (TGFβ-1), fibronectin containing an extra domain A (fibronectin EDA+), and plasminogen activator inhibitor 1 (PAI1) as markers of fibrotic activity. The presence of matrix proteins is measured via immunofluorescent staining of frozen kidney sections with antibodies to matrix proteins induced by TGFβ-1 such as fibronectin EDA+, collagen I, PAI1, and tenasin. From the cultured isolated glomeruli direct measurements of TGFβ-1, PAI1, and fibronectin secreted into the culture supernatant can be determined via ELISAs (enzyme-linked immunoabsorbent assay). Glomeruli from samples in each group can be used to extract mRNA and the message levels for TGFβ-1, GADPH, collagen I, collagen III, fibronectin, and PAI1 determined by Northern analysis. As an indicator of gross histological changes, PAS (periodic acid-Schiff) stained paraffin sections are graded on the basis of their pathological matrix scores. Values are compared between PBS-treated, negative fibrotic control animals; ATS-treated, non-drug treated, positive fibrotic control animals; and the ATS-treated, drug-treated animals to determine the degree to which the fibrotic process is inhibited by somatostatin or the somatostatin agonist.

OTHER EMBODIMENTS

The foregoing description has been limited to specific embodiments of this invention. It will be apparent, however, that variations and modifications may be made to the invention, with the attainment of some or all of the advantages of the invention. Such embodiments are also within the scope of the following claims.

What is claimed is:

1. A method of inhibiting fibrosis in a patient said method comprising administering a therapeutically effective amount of somatastatin or a somatastatin agonist to said patient, wherein said fibrosis is in the kidney, in the lung, in the liver, in the skin, of the central nervous system, in bone or bone marrow, in the cardiovascular system, in an endocrine organ or in the gastro-intestinal system.

2. A method of inhibiting fibrosis in a patient said method comprising administering a therapeutically effective amount of somatostatin or a somatostatin agonist to said patient, wherein said fibrosis is induced by chemotherapy, induced by radiation, induced by a drug or a combination of drugs, induced by a disease state, induced by an environmental or an industrial factor, induced by an immune reaction, or induced by a wound.

3. A method of claim 1, wherein said somatostatin agonist is administered parenterally.

4. A method of claim 3, wherein said somatostatin agonist is administered in a sustained release formulation.

5. A method of claim 1, wherein said somatostatin agonist is administered parenterally.

6. A method of claim 5, wherein said somatostatin agonist is administered in a sustained release formulation.

7. A method of claim 1, wherein said somatostatin agonist is administered topically or orally.

8. A method according to claim 1 wherein the fibrotic disorder in the kidney is glomerulonephritis, diabetic nephropathy, allograft rejection or HIV nephropathy; the fibrotic disorder in the lung is idiopathic fibrosis or autoimmune fibrosis; the fibrotic disorder in the liver is cirrhosis or veno-occlusive disease; the fibrotic disorder in the skin is systemic sclerosis, keloids, burn scars or eosinophilia-myalgia syndrome and the fibrotic disorder in the central nervous system is intraocular fibrosis.

9. A method according to claim 2 wherein the fibrosis induced by chemotherapy is in the kidney, in the lung, in the liver, in the skin, of the central nervous system, in bone or bone marrow, in the cardiovascular system, in an endocrine organ or in the gastro-intestinal system.

10. A method according to claim 2 wherein the fibrosis induced by radiation is in the kidney, in the lung, in the liver, in the skin, of the central nervous system, in bone or bone marrow, in the cardiovascular system, in an endocrine organ or in the gastro-intestinal system.

11. A method of inhibiting over-expression of TGF-β which comprises administering to a subject an effective amount of somatostatin or a somatostatin agonist, or a pharmaceutically acceptable salt thereof.

12. A method according to claim 11 wherein a somatostatin agonist or a pharmaceutically acceptable salt thereof is administered.

13. A method according to claim 12 wherein the somatostatin agonist has a higher binding affinity for human somatostatin sub-type receptor 1, has a higher binding affinity for human somatostatin sub-type receptor 2, has a higher binding affinity for human somatostatin sub-type receptor 3, has a higher binding affinity for human somatostatin sub-type receptor 4, or has a higher binding affinity for human somatostatin sub-type receptor 5.

14. A method according to claim 12 wherein the somatostatin agonist has a higher binding affinity for two or more of human somatostatin sub-type receptor 1, human somatostatin sub-type receptor 2, human somatostatin sub-type receptor 3, human somatostatin sub-type receptor 4 or human somatostatin sub-type receptor 5.

15. A method according to claim 12 wherein the somatostatin agonist is

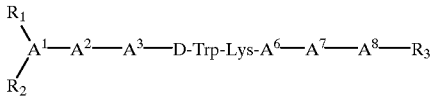

or a pharmaceutically acceptable salt thereof, wherein
$A^1$ is a D- or L- isomer of Ala, Leu, Ile, Val, Nle, Thr, Ser, J-Nal, J-Pal, Trp, Phe, 2,4-dichloro-Phe, pentafluoro-Phe, p-X-Phe, or o-X-Phe, wherein X is $CH_3$, Cl, Br, F, OH, $OCH_3$ or $NO_2$;
$A^2$ is Ala, Leu, Ile, Val, Nle, Phe, J-Nal, pyridyl-Ala, Trp, 2,4-dichloro-Phe, pentafluoro-Phe, o-X-Phe, or p-X-Phe, wherein X is $CH_3$, Cl, Br, F, OH, $OCH_3$ or $NO_2$;
$A^3$ is pyridyl-Ala, Trp, Phe, J-Nal, 2,4-dichloro-Phe, pentafluoro-Phe, o-X-Phe, or p-X-Phe, wherein X is $CH_3$, Cl, Br, F, OH, $OCH_3$ or $NO_2$;
$A^6$ is Val, Ala, Leu, Ile, Nle, Thr, Abu, or Ser;
$A^7$ is Ala, Leu, Ile, Val, Nle, Phe, J-Nal, pyridyl-Ala, Trp, 2,4-dichloro-Phe, pentafluoro-Phe, o-X-Phe, or p-X-Phe, wherein X is $CH_3$, Cl, Br, F, OH, $OCH_3$ or $NO_2$;
$A^8$ is a D- or L-isomer of Ala, Leu, Ile, Val, Nle, Thr, Ser, Phe, J-Nal, pyridyl-Ala, Trp, 2,4-dichloro-Phe, pentafluoro-Phe, p-X-Phe, or o-X-Phe, wherein X is $CH_3$, Cl, Br, F, OH, $OCH_3$ or $NO_2$;
each $R_1$ and $R_2$, independently, is H, lower acyl or lower alkyl; and $R_3$ is OH or $NH_2$; provided that at least one of $A^1$ and $A^8$ and one of $A^2$ and $A^7$ must be an aromatic amino acid; and further provided that $A^1$, $A^2$, $A^7$ and $A^8$ cannot all be aromatic amino acids.

16. A method according to claim 12 wherein the somatostatin agonist is
H-D-Phe-p-chloro-Phe-Tyr-D-Trp-Lys-Thr-Phe-Thr-$NH_2$;
H-D-Phe-p-$NO_2$-Phe-Tyr-D-Trp-Lys-Val-Phe-Thr-$NH_2$;
H-D-Nal-p-chloro-Phe-Tyr-D-Trp-Lys-Val-Phe-Thr-$NH_2$;
H-D-Phe-Phe-Phe-D-Trp-Lys-Thr-Phe-Thr-$NH_2$;
H-D-Phe-Phe-Tyr-D-Trp-Lys-Val-Phe-Thr-$NH_2$;
H-D-Phe-p-chloro-Phe-Tyr-D-Trp-Lys-Val-Phe-Thr-$NH_2$;
H-D-Phe-Ala-Tyr-D-Trp-Lys-Val-Ala-J-D-Nal-$NH_2$;
D-Phe-Cys-Phe-D-Trp-Lys-Thr-Cys-b-Nal-$NH_2$;
D-Phe-Cys-Tyr-D-Trp-Lys-Thr-Cys-b-Nal-$NH_2$;
D-b-Nal-Cys-Phe-D-Trp-Lys-Thr-Cys-Thr-$NH_2$;
D-Phe-Cys-Tyr-D-Trp-Lys-Thr-Pen-Thr-$NH_2$;
D-Phe-Cys-Phe-D-Trp-Lys-Thr-Pen-Thr-$NH_2$;
D-Phe-Cys-Tyr-D-Trp-Lys-Thr-Pen-Thr-OH;
D-Phe-Cys-Phe-D-Trp-Lys-Thr-Pen-Thr-OH;
Gly-Pen-Phe-D-Trp-Lys-Thr-Cys-Thr-OH;
Phe-Pen-Tyr-D-Trp-Lys-Thr-Cys-Thr-OH;
Phe-Pen-Phe-D-Trp-Lys-Thr-Pen-Thr-OH;
H-D-Phe-Cys-Phe-D-Trp-Lys-Thr-Cys-Thr-ol;
H-D-Phe-Cys-Phe-D-Trp-Lys-Thr-Cys-Thr-$NH_2$;
H-D-Trp-Cys-Tyr-D-Trp-Lys-Val-Cys-Thr-$NH_2$;
H-D-Trp-Cys-Phe-D-Trp-Lys-Thr-Cys-Thr-$NH_2$;
H-D-Phe-Cys-Tyr-D-Trp-Lys-Val-Cys-Thr-$NH_2$;
H-D-Phe-Cys-Tyr-D-Trp-Lys-Val-Cys-Trp-$NH_2$;
H-D-Phe-Cys-Tyr-D-Trp-Lys-Val-Cys-Thr-$NH_2$;
Ac-D-Phe-Lys*-Tyr-D-Trp-Lys-Val-Asp-Thr-$NH_2$, wherein an amide bridge is between Lys* and Asp;
Ac-hArg(Et)$_2$-Gly-Cys-Phe-D-Trp-Lys-Thr-Cys-Thr-$NH_2$;
Ac-D-hArg(Et)$_2$-Gly-Cys-Phe-D-Trp-Lys-Thr-Cys-Thr-$NH_2$;
Ac-D-hArg(Bu)-Gly-Cys-Phe-D-Trp-Lys-Thr-Cys-Thr-$NH_2$;
Ac-D-hArg(Et)$_2$-Cys-Phe-D-Trp-Lys-Thr-Cys-Thr-$NH_2$;
Ac-L-hArg(Et)$_2$-Cys-Phe-D-Trp-Lys-Thr-Cys-Thr-$NH_2$;
Ac-D-hArg($CH_2CF_3$)$_2$-Cys-Phe-D-Trp-Lys-Thr-Cys-Thr-$NH_2$;
Ac-D-hArg($CH_2CF_3$)$_2$-Gly-Cys-Phe-D-Trp-Lys-Thr-Cys-Thr-$NH_2$;
Ac-D-hArg($CH_2CF_3$)$_2$-Gly-Cys-Phe-D-Trp-Lys-Thr-Cys-Phe-$NH_2$;
Ac-D-hArg($CH_2CF_3$)$_2$-Gly-Cys-Phe-D-Trp-Lys-Thr-Cys-Thr-NHEt;
Ac-L-hArg($CH_2$-$CF_3$)$_2$-Gly-Cys-Phe-D-Trp-Lys-Thr-Cys-Thr-$NH_2$;
Ac-D-hArg($CH_2CF_3$)$_2$-Gly-Cys-Phe-D-Trp-Lys (Me) -Thr-Cys-Thr-$NH_2$;
Ac-D-hArg($CH_2CF_3$)$_2$-Gly-Cys-Phe-D-Trp-Lys (Me) -Thr-Cys-Thr-NHEt;
Ac-hArg($CH_3$, hexyl)-Gly-Cys-Phe-D-Trp-Lys-Thr-Cys-Thr-$NH_2$;
H-hArg(hexyl$_2$) -Gly-Cys-Phe-D-Trp-Lys-Thr-Cys-Thr-$NH_2$;
Ac-D-hArg(Et)$_2$-Gly-Cys-Phe-D-Trp-Lys-Thr-Cys-NHEt;
Ac-D-hArg(Et)$_2$-Gly-Cys-Phe-D-Trp-Lys-Thr-Cys-Phe-$NH_2$;
Propionyl-D-hArg(Et)$_2$-Gly-Cys-Phe-D-Trp-Lys(iPr)-Thr-Cys-Thr-$NH_2$;
Ac-D-J-Nal-Gly-Cys-Phe-D-Trp-Lys-Thr-Cys-Gly-hArg (Et)$_2$-$NH_2$;
Ac-D-Lys(iPr)-Gly-Cys-Phe-D-Trp-Lys-Thr-Cys-Thr-$NH_2$;
Ac-D-hArg($CH_2CF_3$)$_2$-D-hArg ($CH_2CF_3$) $_2$-Gly-Cys-Phe-D-Trp-Lys-Thr-Cys-Thr-$NH_2$;
Ac-D-hArg($CH_2CF_3$)$_2$-D-hArg ($CH_2CF_3$) $_2$-Gly-Cys-Phe-D-Trp-Lys-Thr-Cys-Phe-$NH_2$;
Ac-D-hArg(Et)$_2$-D-hArg(Et)$_2$-Gly-Cys-Phe-D-Trp-Lys-Thr-Cys-Thr-$NH_2$;
Ac-Cys-Lys-Asn-4-Cl-Phe-Phe-D-Trp-Lys-Thr-Phe-Thr-Ser-D-Cys-$NH_2$;
Bmp-Tyr-D-Trp-Lys-Val-Cys-Thr-$NH_2$;
Bmp-Tyr-D-Trp-Lys-Val-Cys-Phe-$NH_2$;
Bmp-Tyr-D-Trp-Lys-Val-Cys-p-Cl-Phe-$NH_2$;
Bmp-Tyr-D-Trp-Lys-Val-Cys-b-Nal-$NH_2$;
H-D-b-Nal-Cys-Tyr-D-Trp-Lys-Val-Cys-Thr-$NH_2$;
H-D-Phe-Cys-Tyr-D-Trp-Lys-Abu-Cys-Thr-$NH_2$;
H-D-Phe-Cys-Tyr-D-Trp-Lys-Abu-Cys-b-Nal-$NH_2$;
H-pentafluoro-D-Phe-Cys-Tyr-D-Trp-Lys-Val-Cys-Thr-$NH_2$;
Ac-D-b-Nal-Cys-pentafluoro-Phe-D-Trp-Lys-Val-Cys-Thr-$NH_2$;
H-D-b-Nal-Cys-Tyr-D-Trp-Lys-Val-Cys-b-Nal-$NH_2$;
H-D-Phe-Cys-Tyr-D-Trp-Lys-Val-Cys-b-Nal-$NH_2$;
H-D-b-Nal-Cys-Tyr-D-Trp-Lys-Abu-Cys-Thr-$NH_2$;
H-D-p-Cl-Phe-Cys-Tyr-D-Trp-Lys-Abu-Cys-Thr-$NH_2$;
Ac-D-p-Cl-Phe-Cys-Tyr-D-Trp-Lys-Abu-Cys-Thr-$NH_2$;
H-D-Phe-Cys-b-Nal-D-Trp-Lys-Val-Cys-Thr-$NH_2$;
H-D-Phe-Cys-Tyr-D-Trp-Lys-Cys-Thr-$NH_2$;
cyclo (Pro-Phe-D-Trp-N-Me-Lys-Thr-Phe);
cyclo (Pro-Phe-D-Trp-N-Me-Lys-Thr-Phe);

cyclo (Pro-Phe-D-Trp-Lys-Thr-N-Me-Phe);
cyclo (N-Me-Ala-Tyr-D-Trp-Lys-Thr-Phe);
cyclo (Pro-Tyr-D-Trp-Lys-Thr-Phe);
cyclo (Pro-Phe-D-Trp-Lys-Thr-Phe);
cyclo (Pro-Phe-L-Trp-Lys-Thr-Phe);
cyclo (Pro-Phe-D-Trp(F)-Lys-Thr-Phe);
cyclo (Pro-Phe-Trp(F)-Lys-Thr-Phe);
cyclo (Pro-Phe-D-Trp-Lys-Ser-Phe);
cyclo (Pro-Phe-D-Trp-Lys-Thr-p-Cl-Phe);
cyclo (D-Ala-N-Me-D-Phe-D-Thr-D-Lys-Trp-D-Phe);
cyclo (D-Ala-N-Me-D-Phe-D-Val-Lys-D-Trp-D-Phe);
cyclo (D-Ala-N-Me-D-Phe-D-Thr-Lys-D-Trp-D-Phe);
cyclo (D-Abu-N-Me-D-Phe-D-Val-Lys-D-Trp-D-Tyr);
cyclo (Pro-Tyr-D-Trp-t-4-AchxAla-Thr-Phe);
cyclo (Pro-Phe-D-Trp-t-4-AchxAla-Thr-Phe);
cyclo (N-Me-Ala-Tyr-D-Trp-Lys-Val-Phe);
cyclo (N-Me-Ala-Tyr-D-Trp-t-4-AchxAla-Thr-Phe);
cyclo (Pro-Tyr-D-Trp-4-Amphe-Thr-Phe);
cyclo (Pro-Phe-D-Trp-4-Amphe-Thr-Phe);
cyclo (N-Me-Ala-Tyr-D-Trp-4-Amphe-Thr-Phe);
cyclo (Asn-Phe-Phe-D-Trp-Lys-Thr-Phe-Gaba);
cyclo (Asn-Phe-Phe-D-Trp-Lys-Thr-Phe-Gaba-Gaba);
cyclo (Asn-Phe-D-Trp-Lys-Thr-Phe);
cyclo (Asn-Phe-Phe-D-Trp-Lys-Thr-Phe-NH($CH_2$)$_4$CO);
cyclo (Asn-Phe-Phe-D-Trp-Lys-Thr-Phe-b-Ala);
cyclo (Asn-Phe-Phe-D-Trp-Lys-Thr-Phe-D-Glu)-OH;
cyclo (Phe-Phe-D-Trp-Lys-Thr-Phe);
cyclo (Phe-Phe-D-Trp-Lys-Thr-Phe-Gly);
cyclo (Phe-Phe-D-Trp-Lys-Thr-Phe-Gaba);
cyclo (Asn-Phe-Phe-D-Trp-Lys-Thr-Phe-Gly);
cyclo (Asn-Phe-Phe-D-Trp(F)-Lys-Thr-Phe-Gaba);
cyclo (Asn-Phe-Phe-D-Trp($NO_2$)-Lys-Thr-Phe-Gaba);
cyclo (Asn-Phe-Phe-Trp(Br)-Lys-Thr-Phe-Gaba);
cyclo (Asn-Phe-Phe-D-Trp-Lys-Thr-Phe(I)-Gaba);
cyclo (Asn-Phe-Phe-D-Trp-Lys-Thr-Tyr(But)-Gaba);
cyclo (Bmp-Lys-Asn-Phe-Phe-D-Trp-Lys-Thr-Phe-Thr-Pro-Cys)-OH;
cyclo (Bmp-Lys-Asn-Phe-Phe-D-Trp-Lys-Thr-Phe-Thr-Pro-Cys)-OH;
cyclo (Bmp-Lys-Asn-Phe-Phe-D-Trp-Lys-Thr-Phe-Thr-Tpo-Cys)-OH;
cyclo (Bmp-Lys-Asn-Phe-Phe-D-Trp-Lys-Thr-Phe-Thr-MeLeu-Cys)-OH;
cyclo (Phe-Phe-D-Trp-Lys-Thr-Phe-Phe-Gaba);
cyclo (Phe-Phe-D-Trp-Lys-Thr-Phe-D-Phe-Gaba);
cyclo (Phe-Phe-D-Trp(5F)-Lys-Thr-Phe-Phe-Gaba);
cyclo (Asn-Phe-Phe-D-Trp-Lys (Ac) -Thr-Phe-NH-($CH_2$)$_3$-CO);
cyclo (Lys-Phe-Phe-D-Trp-Lys-Thr-Phe-Gaba);
cyclo (Lys-Phe-Phe-D-Trp-Lys-Thr-Phe-Gaba);
cyclo (Orn-Phe-Phe-D-Trp-Lys-Thr-Phe-Gaba);
D-b-Nal-Cys-Tyr-D-Trp-Lys-Thr-Cys-Thr-$NH_2$;
H-Cys-Phe-Phe-D-Trp-Lys-Thr-Phe-Cys-$NH_2$;

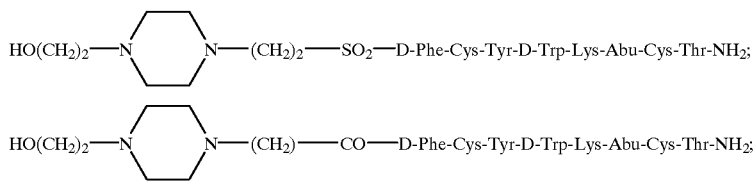

or D-Phe-cyclo(Cys-Phe-D-Trp-Lys-Thr-Cys)-Thr-ol; or a pharmaceutically acceptable salt thereof.

17. A method according to claim 1 wherein the somatostatin agonist has a higher binding affinity for human somatostatin sub-type receptor 1, has a higher binding affinity for human somatostatin sub-type receptor 2, has a higher binding affinity for human somatostatin sub-type receptor 3, has a higher binding affinity for human somatostatin sub-type receptor 4, or has a higher binding affinity for human somatostatin sub-type receptor 5.

18. A method according to claim 1 wherein the somatostatin agonist has a higher binding affinity for two or more of human somatostatin sub-type receptor 1, human somatostatin sub-type receptor 2, human somatostatin sub-type receptor 3, human somatostatin sub-type receptor 4 or human somatostatin sub-type receptor 5.

19. A method according to claim 1 wherein the somatostatin agonist is

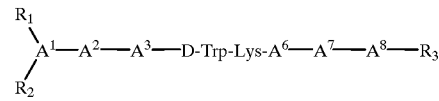

or a pharmaceutically acceptable salt thereof, wherein
$A^1$ is a D- or L- isomer of Ala, Leu, Ile, Val, Nle, Thr, Ser, b-Nal, b-Pal, Trp, Phe, 2,4-dichloro-Phe, pentafluoro-Phe, p-X-Phe, or o-X-Phe, wherein X is $CH_3$, Cl, Br, F, OH, $OCH_3$ or $NO_2$;
$A^2$ is Ala, Leu, Ile, Val, Nle, Phe, b-Nal, pyridyl-Ala, Trp, 2,4-dichloro-Phe, pentafluoro-Phe, o-X-Phe, or p-X-Phe, wherein X is $CH_3$, Cl, Br, F, OH, $OCH_3$ or $NO_2$;
$A^3$ is pyridyl-Ala, Trp, Phe, b-Nal, 2,4-dichloro-Phe, pentafluoro-Phe, o-X-Phe, or p-X-Phe, wherein X is $CH_3$, Cl, Br, F, OH, $OCH_3$ or $NO_2$;
$A^6$ is Val, Ala, Leu, Ile, Nle, Thr, Abu, or Ser;
$A^7$ is Ala, Leu, Ile, Val, Nle, Phe, b-Nal, pyridyl-Ala, Trp, 2,4-dichloro-Phe, pentafluoro-Phe, o-X-Phe, or p-X-Phe, wherein X is $CH_3$, Cl, Br, F, OH, $OCH_3$ or $NO_2$;
$A^8$ is a D- or L-isomer of Ala, Leu, Ile, Val, Nle, Thr, Ser, Phe, b-Nal, pyridyl-Ala, Trp, 2,4-dichloro-Phe, pentafluoro-Phe, p-X-Phe, or o-X-Phe, wherein X is $CH_3$, Cl, Br, F, OH, $OCH_3$ or $NO_2$;
each $R_1$ and $R_2$, independently, is H, lower acyl or lower alkyl; and $R_3$ is OH or $NH_2$; provided that at least one of $A^1$ and $A^1$ and one of $A^2$ and $A^7$ must be an aromatic amino acid; and further provided that $A^1$, $A^2$, $A^7$ and $A^8$ cannot all be aromatic amino acids.

20. A method according to claim 1 wherein the somatostatin agonist is
H-D-Phe-p-chloro-Phe-Tyr-D-Trp-Lys-Thr-Phe-Thr-$NH_2$;
H-D-Phe-p-$NO_2$-Phe-Tyr-D-Trp-Lys-Val-Phe-Thr-$NH_2$;
H-D-Nal-p-chloro-Phe-Tyr-D-Trp-Lys-Val-Phe-Thr-$NH_2$;
H-D-Phe-Phe-Phe-D-Trp-Lys-Thr-Phe-Thr-$NH_2$;
H-D-Phe-Phe-Tyr-D-Trp-Lys-Val-Phe-Thr-$NH_2$;
H-D-Phe-p-chloro-Phe-Tyr-D-Trp-Lys-Val-Phe-Thr-$NH_2$;
H-D-Phe-Ala-Tyr-D-Trp-Lys-Val-Ala-b-D-Nal-$NH_2$;

D-Phe-Cys-Phe-D-Trp-Lys-Thr-Cys-b-Nal-NH$_2$;
D-Phe-Cys-Tyr-D-Trp-Lys-Thr-Cys-b-Nal-NH$_2$;
D-b-Nal-Cys-Phe-D-Trp-Lys-Thr-Cys-Thr-NH$_2$;
D-Phe-Cys-Tyr-D-Trp-Lys-Thr-Pen-Thr-NH$_2$;
D-Phe-Cys-Phe-D-Trp-Lys-Thr-Pen-Thr-NH$_2$;
D-Phe-Cys-Tyr-D-Trp-Lys-Thr-Pen-Thr-OH;
D-Phe-Cys-Phe-D-Trp-Lys-Thr-Pen-Thr-OH;
Gly-Pen-Phe-D-Trp-Lys-Thr-Cys-Thr-OH;
Phe-Pen-Tyr-D-Trp-Lys-Thr-Cys-Thr-OH;
Phe-Pen-Phe-D-Trp-Lys-Thr-Pen-Thr-OH;
H-D-Phe-Cys-Phe-D-Trp-Lys-Thr-Cys-Thr-ol;
H-D-Phe-Cys-Phe-D-Trp-Lys-Thr-Cys-Thr-NH$_2$;
H-D-Trp-Cys-Tyr-D-Trp-Lys-Val-Cys-Thr-NH$_2$;
H-D-Trp-Cys-Phe-D-Trp-Lys-Thr-Cys-Thr-NH$_2$;
H-D-Phe-Cys-Tyr-D-Trp-Lys-Val-Cys-Thr-NH$_2$;
H-D-Phe-Cys-Tyr-D-Trp-Lys-Val-Cys-Trp-NH$_2$;
H-D-Phe-Cys-Tyr-D-Trp-Lys-Val-Cys-Thr-NH$_2$;
Ac-D-Phe-Lys*-Tyr-D-Trp-Lys-Val-Asp-Thr-NH$_2$, wherein an amide bridge is between Lys* and Asp;
Ac-hArg(Et)$_2$-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NH$_2$;
Ac-D-hArg(Bu)-Gly-Cys-Phe-D-Trp-Lys-Thr-Cys-Thr-NH$_2$;
Ac-D-hArg(Et)$_2$-Cys-Phe-D-Trp-Lys-Thr-Cys-Thr-NH$_2$;
Ac-L-hArg(Et)$_2$-Cys-Phe-D-Trp-Lys-Thr-Cys-Thr-NH$_2$;
Ac-D-hArg(CH$_2$CF$_3$)$_2$-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Thr-NH$_2$;
Ac-D-hArg (CH$_2$CF$_3$)$_2$-Gly-Cys-Phe-D-Trp-Lys-Thr-Cys-Phe-NH$_2$;
Ac-D-hArg (CH$_2$CF$_3$)$_2$-Gly-Cys-Phe-D-Trp-Lys-Thr-Cys-Thr-NHEt;
Ac-L-hArg(CH$_2$-CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys(Me)-Thr-Cys-Thr-NH$_2$;
Ac-D-hArg (CH$_2$CF$_3$)$_2$-Gly-Cys-Phe-D-Trp-Lys (Me) -Thr-Cys-Thr-NHEt;
Ac-hArg(CH$_3$, hexyl)-Gly-Cys-Phe-D-Trp-Lys-Thr-Cys-Thr-NH$_2$;
H-hArg(hexyl$_2$)-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NHEt;
Ac-D-hArg(Et)$_2$-Gly-Cys-Phe-D-Trp-Lys-Thr-Cys-Phe-NH$_2$;
Propionyl-D-hArg(Et)$_2$-Gly-Cys-Phe-D-Trp-Lys(iPr)-Thr-Cys-Thr-NH$_2$;
Ac-D-J-Nal-Gly-Cys-Phe-D-Trp-Lys-Thr-Cys-Gly-hArg (Et)$_2$-NH$_2$;
Ac-D-Lys(iPr)-Gly-Cys-Phe-D-Trp-Lys-Thr-Cys-Thr-NH$_2$;
Ac-D-hArg(CH$_2$CF$_3$)$_2$-D-hArg (CH$_2$CF$_3$)$_2$-Gly-Cys-Phe-D-Trp-Lys-Thr-Cys-Thr-NH$_2$;
Ac-D-hArg(CH$_2$CF$_3$)$_2$-D-hArg (CH$_2$CF$_3$)$_2$-Gly-Cys-Phe-D-Trp-Lys-Thr-Cys-Phe-NH$_2$;
Ac-D-hArg(Et)$_2$-D-hArg(Et)$_2$-Gly-Cys-Phe-D-Trp-Lys-Thr-Cys-Thr-NH$_2$;
Ac-Cys-Lys-Asn-4-Cl-Phe-Phe-D-Trp-Lys-Thr-Phe-Thr-Ser-D-Cys-NH$_2$;
Bmp-Tyr-D-Trp-Lys-Val-Cys-Thr-NH$_2$;
Bmp-Tyr-D-Trp-Lys-Val-Cys-Phe-NH$_2$;
Bmp-Tyr-D-Trp-Lys-Val-Cys-p-Cl-Phe-NH$_2$;
Bmp-Tyr-D-Trp-Lys-Val-Cys-b-Nal-NH$_2$;
H-D-b-Nal-Cys-Tyr-D-Trp-Lys-Val-Cys-Thr-NH$_2$;
H-D-Phe-Cys-Tyr-D-Trp-Lys-Abu-Cys-Thr-NH$_2$;
H-D-Phe-Cys-Tyr-D-Trp-Lys-Abu-Cys-b-Nal-NH$_2$;
H-pentafluoro-D-Phe-Cys-Tyr-D-Trp-Lys-Val-Cys-Thr-NH$_2$;
Ac-D-b-Nal-Cys-pentafluoro-Phe-D-Trp-Lys-Val-Cys-Thr-NH$_2$;
H-D-b-Nal-Cys-Tyr-D-Trp-Lys-Val-Cys-b-Nal-NH$_2$;
H-D-Phe-Cys-Tyr-D-Trp-Lys-Val-Cys-b-Nal-NH$_2$;
H-D-b-Nal-Cys-Tyr-D-Trp-Lys-Abu-Cys-Thr-NH$_2$;
H-D-p-Cl-Phe-Cys-Tyr-D-Trp-Lys-Abu-Cys-Thr-NH$_2$;
Ac-D-p-Cl-Phe-Cys-Tyr-D-Trp-Lys-Abu-Cys-Thr-NH$_2$;
H-D-Phe-Cys-b-Nal-D-Trp-Lys-Val-Cys-Thr-NH$_2$;
H-D-Phe-Cys-Tyr-D-Trp-Lys-Cys-Thr-NH$_2$;
cyclo (Pro-Phe-D-Trp-N-Me-Lys-Thr-Phe);
cyclo (Pro-Phe-D-Trp-N-Me-Lys-Thr-Phe);
cyclo (Pro-Phe-D-Trp-Lys-Thr-N-Me-Phe);
cyclo (N-Me-Ala-Tyr-D-Trp-Lys-Thr-Phe);
cyclo (Pro-Tyr-D-Trp-Lys-Thr-Phe);
cyclo (Pro-Phe-D-Trp-Lys-Thr-Phe);
cyclo (Pro-Phe-L-Trp-Lys-Thr-Phe);
cyclo (Pro-Phe-D-Trp(F)-Lys-Thr-Phe);
cyclo (Pro-Phe-Trp(F)-Lys-Thr-Phe);
cyclo (Pro-Phe-D-Trp-Lys-Ser-Phe);
cyclo (Pro-Phe-D-Trp-Lys-Thr-p-Cl-Phe);
cyclo (D-Ala-N-Me-D-Phe-D-Thr-D-Lys-Trp-D-Phe);
cyclo (D-Ala-N-Me-D-Phe-D-Val-Lys-D-Trp-D-Phe);
cyclo (D-Ala-N-Me-D-Phe-D-Thr-Lys-D-Trp-D-Phe);
cyclo (D-Abu-N-Me-D-Phe-D-Val-Lys-D-Trp-D-Tyr);
cyclo (Pro-Tyr-D-Trp-t-4-AchxAla-Thr-Phe);
cyclo (Pro-Phe-D-Trp-t-4-AchxAla-Thr-Phe);
cyclo (N-Me-Ala-Tyr-D-Trp-Lys-Val-Phe);
cyclo (N-Me-Ala-Tyr-D-Trp-t-4-AchxAla-Thr-Phe);
cyclo (Pro-Tyr-D-Trp-4-Amphe-Thr-Phe);
cyclo (Pro-Phe-D-Trp-4-Amphe-Thr-Phe);
cyclo (N-Me-Ala-Tyr-D-Trp-4-Amphe-Thr-Phe);
cyclo (Asn-Phe-Phe-D-Trp-Lys-Thr-Phe-Gaba);
cyclo (Asn-Phe-Phe-D-Trp-Lys-Thr-Phe-Gaba-Gaba);
cyclo (Asn-Phe-D-Trp-Lys-Thr-Phe);
cyclo (Asn-Phe-Phe-D-Trp-Lys-Thr-Phe-NH(CH$_2$)$_4$CO)
cyclo (Asn-Phe-Phe-D-Trp-Lys-Thr-Phe-b-Ala);
cyclo (Asn-Phe-Phe-D-Trp-Lys-Thr-Phe-D-Glu) -OH;
cyclo (Phe-Phe-D-Trp-Lys-Thr-Phe);
cyclo (Phe-Phe-D-Trp-Lys-Thr-Phe-Gly);
cyclo (Phe-Phe-D-Trp-Lys-Thr-Phe-Gaba);
cyclo (Asn-Phe-D-Trp-Lys-Thr-Phe-Gly);
cyclo (Asn-Phe-Phe-D-Trp(F)-Lys-Thr-Phe-Gaba);
cyclo (Asn-Phe-Phe-D-Trp(NO$_2$)-Lys-Thr-Phe-Gaba);
cyclo (Asn-Phe-Phe-Trp(Br)-Lys-Thr-Phe-Gaba);
cyclo (Asn-Phe-Phe-D-Trp-Lys-Thr-Phe(I)-Gaba);
cyclo (Asn-Phe-Phe-D-Trp-Lys-Thr-Tyr(But)-Gaba);
cyclo (Bmp-Lys-Asn-Phe-Phe-D-Trp-Lys-Thr-Phe-Thr-Pro-Cys)-OH;
cyclo (Bmp-Lys-Asn-Phe-Phe-D-Trp-Lys-Thr-Phe-Thr-Pro-Cys)-OH;
cyclo (Bmp-Lys-Asn-Phe-Phe-D-Trp-Lys-Thr-Phe-Thr-Tpo-Cys)-OH;
cyclo (Bmp-Lys-Asn-Phe-Phe-D-Trp-Lys-Thr-Phe-Thr-MeLeu-Cys)-OH;
cyclo (Phe-Phe-D-Trp-Lys-Thr-Phe-Phe-Gaba);
cyclo (Phe-Phe-D-Trp-Lys-Thr-Phe-D-Phe-Gaba);
cyclo (Phe-Phe-D-Trp(5F)-Lys-Thr-Phe-Phe-Gaba);
cyclo (Asn-Phe-Phe-D-Trp-Lys (Ac) -Thr-Phe-NH- (CH$_2$)$_3$-CO);
cyclo (Lys-Phe-Phe-D-Trp-Lys-Thr-Phe-Gaba);
cyclo (Lys-Phe-Phe-D-Trp-Lys-Thr-Phe-Gaba);
cyclo (Orn-Phe-Phe-D-Trp-Lys-Thr-Phe-Gaba);
D-b-Nal-Cys-Tyr-D-Trp-Lys-Thr-Cys-Thr-NH$_2$;
H-Cys-Phe-Phe-D-Trp-Lys-Thr-Phe-Cys-NH$_2$;

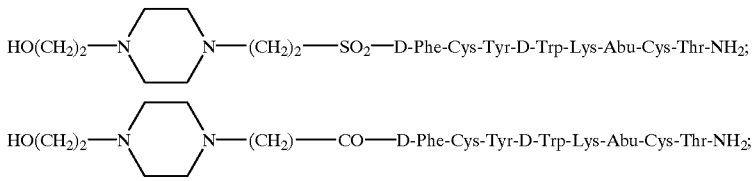

or D-Phe-cyclo(Cys-Phe-D-Trp-Lys-Thr-Cys)-Thr-ol; or a pharmaceutically acceptable salt thereof.

21. A method according to claim 2, wherein the fibrosis induced by a drug or a combination of drugs is in the kidney, in the lung, in the liver, in the skin, of the central nervous system, in bone or bone marrow, in the cardiovascular system, in an endocrine organ, or in the gastro-intestinal system.

22. A method according to claim 2 wherein the fibrosis induced by a disease state is in the kidney, in the lung, in the liver, in the skin, of the central nervous system, in bone or bone marrow, in the cardiovascular system, in an endocrine organ, or in the gastro-intestinal system.

23. A method according to claim 2 wherein the fibrosis induced by an environmental or an industrial factor is in the kidney, in the lung, in the liver, in the skin, of the central nervous system, in bone or bone marrow, in the cardiovascular system, in an endocrine organ, or in the gastro-intestinal system.

24. A method according to claim 2 wherein the fibrosis induced by an immune reaction is in the kidney, in the lung, in the liver, in the skin of the central nervous system, in bone or bone marrow, in the cardiovascular system, in an endocrine organ, in the gastro-intestinal system.

25. A method according to claim wherein the fibrosis induced by a wound is in the kidney, in the lung, in the liver, in the skin, of the central nervous system, in bone or bone marrow, in the cardiovascular system, in an endocrine organ, or in the gastrointestinal system.

26. A pharmaceutical composition useful for inhibiting fibrosis in a patient which comprises a pharmaceutically acceptable carrier and an effective amount of somatostatin or a somatostatin agonist, or a pharmaceutically acceptable salt thereof.

27. A pharmaceutical composition according to claim wherein the composition comprises a somatostatin agonist or a pharmaceutically acceptable salt thereof.

28. A pharmaceutical composition useful for inhibiting overexpression of TGF-β which comprises a pharmaceutically acceptable carrier and an effective amount of somatostatin or a somatostatin agonist, or a pharmaceutically acceptable salt thereof.

29. A pharmaceutical composition according to claim 28 wherein the composition comprises a somatostatin agonist or a pharmaceutically acceptable salt thereof.

* * * * *

UNITED STATES PATENT AND TRADEMARK OFFICE
CERTIFICATE OF CORRECTION

PATENT NO.         : 6,268,342 B1                                         Page 1 of 1
APPLICATION NO. : 09/254097
DATED              : July 31, 2001
INVENTOR(S)        : Michael D. Culler et al.

It is certified that error appears in the above-identified patent and that said Letters Patent is hereby corrected as shown below:

Col. 30, approx. line 11, that portion which reads "to claim wherein" should read -- to claim 2 wherein --

Col. 30, approx. line 21-22, that portion which reads "to claim wherein" should read -- to claim 26 wherein --

Signed and Sealed this

Twenty-fourth Day of October, 2006

JON W. DUDAS
*Director of the United States Patent and Trademark Office*